United States Patent [19]

Stott et al.

[11] Patent Number: 5,198,213

[45] Date of Patent: * Mar. 30, 1993

[54] METHOD OF DISEASE TREATMENT UTILIZING AN IMMUNOLOGICALLY WHEY FRACTION

[75] Inventors: Gerald H. Stott, Emmett, Id.; David O. Lucas, Plymouth, Minn.

[73] Assignee: Protein Technology, Inc., Santa Rosa, Calif.

[*] Notice: The portion of the term of this patent subsequent to Mar. 28, 2006 has been disclaimed.

[21] Appl. No.: 777,194

[22] Filed: Oct. 16, 1991

Related U.S. Application Data

[63] Continuation of Ser. No. 306,817, Feb. 3, 1989, Pat. No. 5,066,491, which is a continuation-in-part of Ser. No. 946,435, Dec. 24, 1986, Pat. No. 4,834,974, which is a continuation-in-part of Ser. No. 818,610, Jan. 13, 1986, Pat. No. 4,816,252, which is a continuation-in-part of Ser. No. 723,612, Apr. 15, 1985, abandoned.

[51] Int. Cl.⁵ .................. A61K 39/395; A61K 35/20
[52] U.S. Cl. .................................. 424/85.8; 514/2; 514/21; 530/387.1; 530/414; 530/833
[58] Field of Search ............ 424/85.8; 514/2, 21; 530/387, 414, 833, 387.1

[56] References Cited

U.S. PATENT DOCUMENTS

| | | | |
|---|---|---|---|
| 3,128,230 | 4/1964 | Heinbach | 426/86 |
| 3,376,198 | 4/1969 | Peterson et al. | |
| 3,487,064 | 12/1969 | Swanson et al. | 534/417 |
| 3,547,900 | 12/1970 | Dienst et al. | 530/378 |
| 3,553,317 | 1/1971 | Michaelson et al. | 424/87 |
| 3,687,682 | 8/1972 | Scheder | 426/239 |
| 3,687,928 | 8/1972 | Brouwer et al. | 530/366 |
| 3,707,770 | 1/1973 | Timmins et al. | 426/271 |
| 3,791,283 | 2/1974 | Moreno et al. | 530/414 |
| 3,911,108 | 10/1975 | Singh | 424/86 |
| 3,930,039 | 12/1975 | Kiupers | 426/271 |
| 3,969,336 | 7/1976 | Criswell | 530/427 |
| 3,969,337 | 7/1976 | Lauer et al. | 530/427 |
| 3,975,517 | 8/1976 | Wilson | 424/87 |
| 4,042,575 | 8/1977 | Eustache | 435/272 |
| 4,784,850 | 11/1988 | Abraham | 424/87 |
| 4,816,252 | 3/1989 | Stott et al. | 424/85.8 |
| 4,834,974 | 5/1989 | Stott et al. | 530/387 |

FOREIGN PATENT DOCUMENTS

1202979 8/1970 United Kingdom.
1312877 4/1973 United Kingdom.

OTHER PUBLICATIONS

Advertisement, "Concentrated colostrum from whey. New product ends time consuming collection methods," BEEF, Feb., 1987, p. 52.

Arschaffenberg, R. et al., "The nutritive value of colostrum for the calf. 4. The effect of small quantities of colostral whey, dialyzed whey and 'immune lactoglobulins'," Br. J. Nutr. 5: 171 (1951).

Cruywagen, C. W., "Effect of curd forming of colostrum on absorption of immunoglobulin G in newborn calves," J. DairySci. 73(11): 3287 (1990).

(List continued on next page.)

Primary Examiner—Merrell C. Cashion, Jr.
Assistant Examiner—P. L. Touzeau
Attorney, Agent, or Firm—Cooper & Dunham

[57] ABSTRACT

Whey derived from ordinary milk includes a bottom fraction including lactose and minerals, a middle fraction including lower molecular weight proteins, and a top fraction including higher molecular weight proteins. The top whey fraction includes a measurable but low level concentration of immunologically active immunoglobulin plus other pathogen specific antibodies. The whey is ultrafiltered through one or more different process steps to yield a filtered product having a concentration of immunologically active immunoglobulin of at least about seven percent of total solids. The filtered product is periodically tested to verify its activity to a specified microbe. The filtered product is orally administered in a therapeutically effective dose to an animal to treat a disease.

27 Claims, 6 Drawing Sheets

OTHER PUBLICATIONS de Wit, J. N. et al., "Evaluation of functional properties of whey protein concentrates and whey protein isolates. I. Isolation and characterization," Neth. Milk Dairy J. 37: 37 (1983).

Haines, D. M. et al., "Immunoglobulin concentrations in commercially available colostrum supplements for calves," Can. Vet. J. 31: 36 (1990a).

Haines, D. M. et al., Authors' reply to letter of Dennis A. Nelson, Can. Vet. J. 31: 338 (1990b).

Mutilangi., W. A. M. and Kilara, A., "Functional properties of heat-denatured whey proteins. II. Emulsion and foaming properties," Milchwissenschaft 40(7): 391 (1985).

Renner, E. and El-Salam, M. H., *Application of Ultrafiltration in the Dairy Industry*, Elsevier Science Publishers Limited, Barking, Essex, England, pp. 218–226 (1991).

Roy, J. H. B., "Symposium: disease prevention in calves. Factors affecting susceptibility of calves to disease.," J. Dairy Sci. 63: 650 (1980).

METHOD OF DISEASE TREATMENT UTILIZING AN IMMUNOLOGICALLY WHEY FRACTION

This application is a continuation of Ser. No. 306,817, filed Feb. 3, 1989, now U.S. Pat. No. 5,066,491, which is a continuation-in-part of patent application Ser. No. 6/946,435 filed Dec. 24, 1986, now U.S. Pat. No. 4,834,974 which was a continuation-in-part of patent application Ser. No. 6/818,610, filed Jan. 13, 1986 now U.S. Pat. No. 4,816,252 which was a continuation-in-part of U.S. patent application Ser. No. 6/723,612 filed Apr. 15, 1985, now abandoned. The disclosures of patent application Ser. Nos. 818,610 and 946,435 are hereby incorporated by reference.

BACKGROUND OF THE INVENTION

1. Field of the Invention

This invention relates to a method of disease treatment utilizing a therapeutically effective product produced from whey.

2. Description of the Prior Art

As is common with most domestic animals, bovine calves are born without immunity. Passive immunity is transferred on a postpartum basis from a dam (mother) to the newborn calf through an initial mammary gland secretion known as colostrum. This initial colostrum secretion contains rapidly diminishing levels of immunologically active, large molecular weight proteins known as immunoglobulins (abbreviated below as "Ig"). These Ig molecules possess antibody properties, are actively produced by mature animals, and enhance immunity to infection by bacteria, viruses or parasites. At birth, a calf lacks Ig in its blood serum. Only as a direct response to ingestion and absorption of a quantity and quality of Ig from maternal colostrum shortly after birth can a calf's immune system function efficiently.

The first essential element of the natural passive immunity transfer mechanism relates to the characteristics of the maternal colostrum. To achieve ideal passive immunity, the maternal colostrum should contain an adequate concentration of Ig having an appropriate distribution of pathogen specific antibodies and an appropriate concentration of each pathogen specific antibody. If the maternal colostrum contains an insufficient concentration of important pathogen specific antibodies, the calf will absorb an insufficient quantity of these antibodies and will develop a deficient level of immunity to the diseases which such antibodies attack.

The second essential element of the natural passive immunity transfer mechanism is calf-oriented and relates to the quantity and time of colostrum ingestion. As to quantity of ingestion, previous studies have indicated that there is a limit to the volume of colostrum that can be ingested to maximize the level of Ig absorbed into the calf's circulatory system. Consumption of more than two liters of colostrum fails to enhance calf Ig absorption levels to any significant degree. Furthermore, newborn calves rarely ingest more than two liters of liquid within a feeding period. As to the time of ingestion, the permeability of the newborn calf's gut to the large molecular weight Ig molecules diminishes very rapidly after birth as a result of intestinal cell maturation. This well-known natural intestinal mechanism may be referred to as the "critical period of absorption" which defines the short postpartum interval during which the calf must consume and absorb the optimum quantity of ideal potency colostrum to achieve an ideal level of passive immunity. Although colostrum consumption as late as twenty-four hours postpartum may achieve some immune transfer, subsequent colostrum consumption will have very little effect on passive immune levels. Ideally, colostrum ingestion should occur within the first eight hours postpartum.

In practice, a high percentage of calves either consume far less than an ideal quantity and quality of colostrum or fail to consume colostrum within the critical absorption period. The resulting adverse effects due to the lack of immune transfer are demonstrated by high calf death rates, increased susceptibility to disease and reduced growth rate.

At birth, a calf lacks immunity to disease as is demonstrated by the low blood serum antibody concentration. Within approximately six to twelve hours after birth, the calf ingests two liters of colostrum having an ideal Ig concentration and distribution of pathogen specific antibodies. As these large molecular weight Ig or antibody molecules are intestinally absorbed, the blood serum antibody concentration rapidly increases. Several hours after initial colostrum ingestion, the transfer of colostrum Ig molecules from the gut into the calf's bloodstream has been completed. Over the next few days, the blood serum Ig concentration derived from the maternal colostrum gradually declines through normal systemic turnover. Subsequently, the calf's immune system commences active Ig production which replaces the declining supply of colostrum-derived Ig. Ultimately, the calf's immune system achieves a self-sustaining or active Ig production and will maintain an essentially constant blood serum Ig concentration.

Previous research has indicated that a blood serum Ig concentration on the order of twenty milligrams per milliliter or above is highly desirable. Calves possessing such Ig concentrations demonstrate a markedly reduced mortality rate, a high level of resistance to disease and impressively enhanced growth rates in comparison to calves having lower levels of passive immunity.

An ideal immunity transfer dramatically contrasts with a common naturally occurring immunity transfer. Consumption of an insufficient quantity of colostrum or consumption of a low Ig concentration colostrum produces a deficient level of passive immunity transfer. If a calf having this deficient level of passive immunity is exposed to a disease, there is a high probability that it will contract the disease, require expensive medical treatment and may die or lack sufficient growth potential.

Because domestic dairy cattle have been selectively bred for maximum milk production, the passive immunity transfer problems encountered by dairymen are particularly acute. At the onset of lactation, a dairy cow's high milk production volume rapidly dilutes the limited quantity of colostrum Ig molecules. As a result, the concentration of these Ig molecules in the fluid initially consumed by a newborn calf may be far below the level required to achieve an adequate level of passive immunity. Since the typical non-aggressive dairy calf consumes only a comparatively small amount of colostrum during the critical absorption period, the number of Ig molecules present in the calf's gut and available for absorption into the bloodstream is frequently unacceptably low. The resulting passive immunity level fails to provide adequate disease resistance.

To combat the immunity deficiency problems outlined above, some dairymen having small dairy herds manually milk what they believe to be an adequate quantity of colostrum from a dam and force feed it to its newborn calf during the critical absorption period. This labor intensive method of controlling the timing and quantity of colostrum consumption cannot compensate for colostrum having a low Ig concentration or an inadequate spectrum of pathogen specific antibodies. Since only complex, time consuming laboratory tests can measure the colostrum Ig concentration and antibody distribution, these dairymen have no way of verifying that the colostrum which they laboriously obtain and force feed to newborn calves will provide adequate levels of passive immunity.

In large dairy operations, a different tactic has been implemented in an attempt to control the time of colostrum ingestion, the quantity of Ig consumed and the pathogen specific antibody distribution of the colostrum. Milk drawn from a group of dams within twelve hours postpartum is blended together. An appropriate quantity of this blended "colostrum" is fed to each newborn calf. Because dairymen have no way of controlling the Ig concentration or distribution of pathogen specific antibodies in this blended "colostrum," this labor intensive procedure has not achieved satisfactory results.

Another existing technique for enhancing the disease resistance of a calf to a specific disease involves prepartum vaccination of the dam. The vaccination increases the serum blood level concentration of the desired pathogen specific antibody and ultimately yields colostrum having enhanced levels of the desired antibody. After consuming this enhanced colostrum, the calf attains an increased level of immunity, but only to the selected disease.

In laboratory studies, researchers have assayed the Ig concentration and distribution of pathogen specific antibodies in colostrum and have administered controlled quantities of such assayed colostrum to newborn calves at controlled times within the critical absorption period. A direct correlation between these measured colostrum Ig variables and calf disease resistance, death rate, and growth rate has been demostrated. Although these laboratory testing activities have substantially increased the level of knowledge of the natural passive immunity transfer mechanism in animals, they have not solved the immunity transfer problems outlined above by providing a method for positively controlling the Ig concentration and distribution of pathogen specific antibodies in colostrum.

The substantial economic loss suffered by dairymen and others as a direct result of the inability to control the passive immunity transfer mechanism, evidences a strong need for a product or process capable of positively controlling the immunity transfer mechanism.

Calves are highly susceptible to infection by a variety of microbes including the *E. coli* bacteria and the protozoa Cryptosporidia, each of which is capable of inducing severe diarrhea in the calf and of ultimately causing death. While high potency natural colostrum is capable of activating the calves immune system to produce antibodies pathogen specific to the *E. coli* bacteria, natural colostrum is ineffective in causing a calf's immune system to generate antibodies pathogen specific to the protozoa Cryptosporidia.

SUMMARY OF THE INVENTION

It is therefore a major object of the present invention to provide a method of disease treatment utilizing a therapeutically effective product derived from ordinary milk whey where the product possesses verified immunological activity and is capable of treating diseases caused by such microbes.

It is another major object of the present invention to separate the therapeutically effective product from ordinary milk whey having a measurable but low level concentration of immunologically active immunoglobulin by utilizing ultrafiltration possessing techniques.

It is another object of the present invention to provide a method of disease treatment utilizing a therapeutically effective product produced from ordinary milk whey having efficacy in either treating or preventing diseases caused by a variety of microbes.

It is another object of the present invention to provide a method of disease treatment utilizing a therapeutically effective product produced from ordinary milk whey which is effective in treating diseases caused by the *E. coli* bacteria and the protozoa Cryptosporidia.

Briefly stated, the present invention encompasses a method of disease treatment utilizing a therapeutically effective product produced from ordinary milk whey. The whey includes a bottom fraction having lactose and minerals, a middle fraction having lower molecular weight proteins, and a top fraction having higher molecular weight proteins. The whey is derived from ordinary milk and includes in the top fraction a measurable, but low level concentration of immunologically active immunoglobulin with various different pathogen specific antibodies. The whey is ultrafiltered to produce a high protein concentration retentate having a substantially decreased concentration of lactose and minerals. The ultrafiltration procedures are accomplished under thermal conditions which substantially preserve the immunological activity of the immunoglobulin in the whey. The retentate is dried under conditions which substantially preserve the immunological activity of the immunoglobulin in the retentate to produce a filtered product having at least about a seven percent weight concentration of immunologically active immunoglobulin. The filtered product is periodically tested to verify its immunological activity. A therapeutically effective dose of the filtered product is orally administered to an animal to treat the predetermined diseases.

DESCRIPTION OF THE DRAWINGS

The invention is pointed out with particularity in the appended claims. However, other objects and advantages together with the operation of the invention may be better understood by reference to the following detailed description taken in connection with the following illustrations, wherein:

DESCRIPTION OF THE PREFERRED EMBODIMENT

Figure 1:
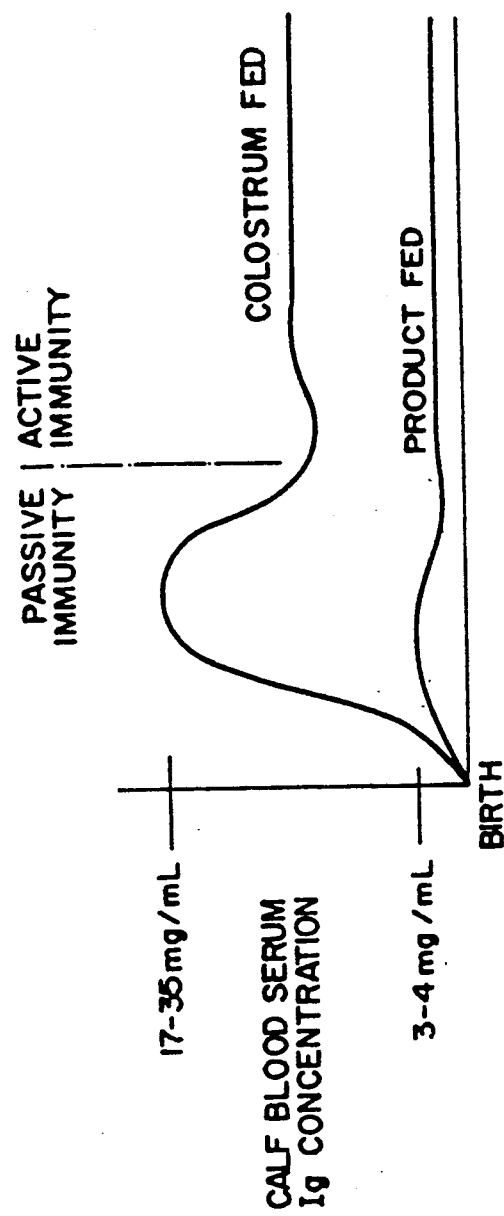
FIG. 1 graphically compares the calf blood serum Ig concentration achieved by natural colostrum with the blood serum Ig concentration achieved by the whey-derived product produced according to the present invention.

In order to better illustrate the advantages of the invention and its contributions to the art, a preferred embodiment of the inventive process and product will now be described in detail.

Milk secreted by domestic animals such as dairy cows includes long term but low level concentrations of Ig which has no measurable effect on passive immunity when ingested. The present invention relates to a process for extracting and concentrating the Ig molecules found in whey under carefully controlled conditions to preserve the immunological activity of the structurally delicate, thermosensitive Ig molecules. The terms "immunological activity" or "immunologically active" as used in connection with Ig molecules refers to the ability of the Ig molecules to bind to antigens. Such concentrated, immunologically active Ig molecules can then be fed to newborn calves shortly postpartum as either a colostrum substitute or supplement to exert positive control over the natural passive immunity transfer mechanism. The invention recognizes and takes advantage of the fact that Ig molecules constitute the largest molecules in milk and that a limited number of these molecules remain in the low economic value whey byproduct of the cheese making process. Although approximately 85,000,000 metric tons of whey is created annually as a byproduct of cheese production worldwide, about 34,000,000 metric tons of whey cannot be economically utilized. The whey byproduct useful in practicing the present invention can therefore be obtained at minimal cost and will reduce the burden of disposing the unwanted whey.

In one conventional cheese production facility, raw milk is processed to create curd, the primary cheese constituent, and a liquid whey byproduct. The raw milk input product includes approximately fourteen percent solids. Four percent constitutes proteins, including high molecular weight immunologically active Ig proteins and other immunologically active whey protein components. A high percentage of the milk protein component is precipitated out as casein during the cheese making process. The resulting whey byproduct may include approximately six percent solids, seventy percent of which represents lactose and thirty percent of which represents proteins, minerals and fat. The residual whey protein component in general comprises a mixture of lactalbumin, lactoglobulin, serum albumin, immunoglobulins (Ig) and polypeptides.

The term "whey" as used in the description of the invention includes both the liquid whey byproduct of the cheese making process as well as milk from which casein has been removed.

An objective of the present invention is to process raw milk and the resulting whey byproduct under carefully controlled conditions to radically increase the Ig concentration of the ultimate processed product in comparison to the minimal, immunologically ineffective Ig concentration in the raw milk input product. This process must be accomplished under carefully controlled conditions to avoid substantially reducing the immunological activity of the Ig molecules.

Numerous prior art techniques exist for producing dry concentrated protein extract from whey. This protein extract is commonly referred to as whey protein concentrate or "WPC." Such prior art protein extraction and concentration techniques are primarily concerned with preserving the food qualities of the WPC, e.g., taste, flavor, solubility, etc. Although these prior art whey and WPC extraction techniques are capable of producing useful food products, they expose the raw milk, whey or resulting WPC to: 1) excessive thermal (time/temperature) conditions, 2) excessive bacterial activity, or 3) excessive enzymes added in processing or resulting from such bacterial activity.

The specific process steps capable of separating Ig molecules from raw milk and producing an end product having highly concentrated levels of immunologically active Ig will now be discussed in detail.

A homogeneous volume of raw milk is typically obtained from one or more herds of dairy cattle located within a specific geographic region. This raw milk is flash pasteurized, for example, by rapidly elevating its temperature to approximately 160° F., maintaining it at that temperature for from fifteen seconds to as long as twenty seconds, and rapidly decreasing the milk temperature. Testing has indicated that the comparatively rapid temperature rise, the short time at elevated temperatures and the comparatively rapid temperature reduction accomplished during this flash pasteurization step adequately standardizes and controls microbial activity in the milk without significantly affecting the immunological activity of the Ig in the milk.

If significant deviations are made from the above stated flash pasteurization time/temperature parameters as is common with other well known but longer duration pasteurization procedures, the immunological activity of the milk Ig molecules will be substantially reduced or destroyed. Such procedures should therefore be avoided while practicing the process of the present invention.

In certain instances, it is possible to implement a second flash pasteurization step during whey processing operations. The implementation of a second flash pasteurization step will tend to reduce the overall immunological activity of the Ig molecules, but still results in a useful level of Ig immunological activity. The utilization of a third flash pasteurization step has been found to virtually totally destroy the immunological activity of the Ig molecules and should therefore be avoided in most circumstances. The immunological activity of the Ig molecules should be carefully tested following each pasteurization step during the initial implementation of the inventive process to verify continuing Ig immunological activity. The results of such testing will indicate whether any pasteurization step should be modified or eliminated.

After completion of the pasteurization step, the milk is exposed to an appropriate cheese producing starter such as lactobacillus. As is common practice in cheese processing, the temperature in the cheese formation vat is generally adjusted to and maintained at about 86° F. to 90° F. for approximately two hours until a desired degree of curd formation has occurred. At that time, the cheese vat temperature is increased to approximately 102° F. and the whey is drained off, a procedure typically requiring approximately thirty to forty-five minutes. The whey byproduct is immediately transferred to a clarifier or separator at a temperature of about 100° F. where the fat and casein particles components of the whey byproduct are removed. At this point, the clarified whey may be stored temporarily at 40° F. to restrict bacterial activity or may be immediately transported to an ultrafiltration system. During ultrafiltration, the whey is heated to and maintained at a temperature of between about 120° F. to 130° F. The specific process parameters recited above have been found to substantially maintain Ig immunological activity. In implementing the process of the present invention, the above stated time and temperature parameters may be varied as necessary as long as the Ig immunological activity is substantially maintained as verified by test procedures of the type described below. It is highly desirable that the whey or whey byproduct not be exposed to temperatures exceeding 130° F. during either the cheese making process or during ultrafiltration processing.

Ultrafiltration techniques have been utilized for a number of years to separate the various groups of larger molecular weight protein molecules from the smaller molecular weight, nonprotein components of clarified whey. Similar ultrafiltration techniques are followed in implementing the process of the present invention. The warm clarified whey is directed to a first ultrafiltration module designated as "$UF_1$." In one embodiment, module $UF_1$ includes an ultrafiltration membrane permeable to materials having a molecular weight less than about ten thousand Daltons, but impermeable to higher molecular weight materials such as protein molecules. The material retained by the ultrafiltration membrane is referred to as the "retentate," while the material passing through the ultrafiltration membrane is referred to as the "permeate." Undesirable lower molecular weight materials such as lactose, minerals and salts are permeable to the ultrafiltration membrane and are removed from the whey byproduct along with water during the initial ultrafiltration steps.

As the retentate is passed either repeatedly through a single ultrafiltration module or directed to the next in a series of ultrafiltration modules, it becomes more concentrated with solids, its viscosity increases and a polarization phenomenon occurs at the ultrafiltration membranes, rendering them ineffective. Membrane polarization is counteracted by diluting the retentate with water and subjecting the diluted retentate to further ultrafiltration, a process known as diafiltration. This series of ultrafiltration steps is repeated until the retentate contains solids having highly concentrated levels of proteins, preferably as high as seventy to eighty percent proteins. At this point in the procedure, the concentration of the desired Ig segment of the protein molecules represents less than ten percent of the total retentate protein composition. Since the smallest of these retentate Ig molecules have molecular weights on the order of one hundred and sixty thousand Daltons or greater and since serum albumin, the next largest retentate protein molecule, possesses a molecular weight on the order of sixty-six thousand Daltons, the partially filtered retentate can be directed through one or more ultrafiltration modules having an ultrafiltration membrane permeable to the serum albumin and other lower molecular weight protein molecules and impermeable to the substantially larger Ig molecules to significantly increase the retentate Ig concentration. Ultrafiltration membranes capable of achieving these objectives are available commercially.

Although the primary ultrafiltration process was described above in connection with a 10,000 Dalton membrane and the secondary ultrafiltration process was described above in connection with a 100,000 Dalton membrane, such specific permeability levels have been utilized merely for the purpose of illustration. The invention can be implemented in many different ways by repeatedly utilizing a single ultrafiltration module, sequentially substituting membranes having differing permeability levels, utilizing a series of ultrafiltration modules having a series of membranes of either increasing or constant permeability, or by using a single ultrafiltration module having a membrane permeability between about 66,000 to 160,000 Daltons. In practice, an ultrafiltration module having a single 100,000 Dalton membrane has been found to work in a satisfactory manner. In view of the objectives and procedures stated above, selection of appropriate ultrafiltration equipment and procedures would be obvious to one of ordinary skill in the art in order to achieve the desired elevated concentrations of the large molecular weight Ig molecules.

It is important to the practice of the present invention that the immunological activity of the Ig molecules be preserved during all processing steps, including the ultrafiltration steps, by appropriate temperature control, by maintenance of conditions to minimize unwanted microbial activity, and by carefully controlling and monitoring heating and pasteurization. In existing cheese processing plants and ultrafiltration plants, very few if any of these safeguards are followed. As a result, existing ultrafiltration plants produce WPC having an Ig component lacking significant immunological activity.

Since destruction of the immunological properties of Ig molecules may not alter molecular size or weight, it is important to the practice of the present invention that substantially all of the Ig molecules remain immunologically active. Desirably only a comparatively small percentage of Ig molecules are immunologically deactivated during processing. Ingestion of an Ig solution having an excessive concentration of immunologically inactive Ig will fail to achieve an effective blood serum concentration of immunologically active Ig in newborn domestic animals. It is therefore important to maintain a relatively high concentration of immunologically active Ig molecules in comparison to immunologically inactive Ig molecules throughout each step of the inventive process to produce a product capable of controlling the transfer of passive immunity.

The product may then be dried by conventional freeze-drying procedures (lyophilization) or spray drying techniques. In most situations, the spray drying procedure is preferred since the equipment is commonly found in most dairy processing plants. Furthermore, this procedure is more efficient, drying the product of the invention at substantially greater rates and at lower cost than is possible with freeze-drying. The resulting dry filtered product can be stored at room temperature.

Since the immunological activity of the Ig is easily destroyed by excessive thermal exposure, but is unaffected by low or freezing temperatures, removal of water from the partially dehydrated ultrafiltration retentate by freeze-drying equipment does not adversely affect the immunological activity of the Ig. A different mechanism prevents significant reduction in the immunological activity of the Ig during spray drying. Although in spray drying equipment the partially dehydrated filtration retentate is exposed to high velocity air at a temperature on the order of 300° F., the temperature of the Ig molecules is maintained at a comparatively low level due to the substantial heat sink effect of the water heat of vaporization. Overall, the spray drying procedure is more economical and produces dry powdered WPC at substantially higher rates than is possible with freeze-drying equipment.

Prior art techniques for partially drying concentrated protein ultrafiltration retentate to produce WPC for use in animal or human food products frequently involve placement of the retentate in a vacuum chamber maintained at elevated temperatures for periods of six to eight hours. Although the flavor and nutritional properties of the vacuum dried WPC may be unaffected by this procedure, the immunological activity of the Ig is completely destroyed. Such retentate drying techniques are therefore unacceptable in implementing the process of the present invention.

Following the retentate drying step, the dry powdered product should be assayed to verify the immunological properties of the resulting Ig, including the distribution and concentration of pathogen specific antibodies in the Ig. The relative concentration of pathogen specific antibodies in various samples of dry filtered product produced by implementing the process of the present invention will have sample to sample variations resulting from the extraction of Ig molecules from different batches of raw milk having differing Ig distributions and concentrations. In practice, each minimum acceptable antibody level would be carefully determined to ensure at least a predetermined level of passive immunity to a specific disease for a calf fed a measured quantity of filtered product at a designated time postpartum.

A test, known as the "EIA" test, measures the activity of pathogen specific antibodies in the filtered product and is described in an article entitled "Quantification of Bovine IgG, IgM and IgA Antibodies To Clostridium Perfringens B-Toxin By Enzyme Immunoassay I. Preparturient Immunization For Enhancement Of Passive Transfer of Immunity." This article was published in *Veterinary Immunology and Immunopathology*, Vol. 4 (1983) at pp. 579-591 and was authored by W. A. Fleenor and G. H. Stott. The disclosure of that article is hereby incorporated by reference. The EIA test procedure discussed in that article is known to persons of ordinary skill in the appropriate field.

The EIA test in combination with the radial immune diffusion test (RID test) is capable of measuring the percentage of Ig molecules which have been immunologically deactivated during the process of the present invention. Although the RID test is capable of measuring the number of Ig molecules in milk, whey or the filtered product, it cannot distinguish between immunologically active and immunologically inactive Ig molecules.

It is therefore desirable to perform a dual analysis of the milk or whey input product by 1) using the EIA test to measure the activity of one or more pathogen specific antibodies in the input product and 2) using the RID test to measure the number of Ig molecules in the input product. The EIA test results divided by the RID test results yield a first set of ratios representative of the relative concentration of each tested pathogen specific antibody to the total number of Ig molecules in the input product, whether such molecules are immunologically active or inactive.

The EIA and RID tests are used in the same way to assay the filtered product. The EIA test results divided by the RID test results produce a second set of ratios representative of the relative concentration of each tested pathogen specific antibody to the total number of Ig molecules in the filtered product, whether such molecules are immunologically active or inactive. Comparison of each of the first set of ratios with each of the second set of ratios will indicate the percentage reduction in the relative concentration of each pathogen specific antibody and is representative of the percentage of Ig molecules which have been immunologically deactivated by the process of the present invention.

The combined EIA/RID test procedures described above therefore represent one technique for verifying that the immunological activity of the Ig molecules has been substantially maintained during implementation of the process of the present invention. A series of related combined test procedures can be applied to the initial and intermediate process steps and to the final product to identify and eliminate process conditions responsible for unacceptable reductions in the immunological activity of Ig molecules. Once the process has been stabilized, it may be possible to discontinue the combined EIA/RID test procedures until specific Ig immunological deactivation problems arise.

Once a complete set of process standards has been established, it may be possible to rely exclusively on the EIA test to monitor the distribution and concentration of pathogen specific antibodies in the filtered product. The concentration of a single pathogen specific antibody may be found to vary in direct proportion to the overall process-induced percentage reduction in Ig immunological activity. If so, that single pathogen specific antibody could be substituted for the combined EIA/RID tests to identify immunological deactivation problems.

Calves are commonly exposed to and require adequate passive immunity to the following pathogens:
1. *Escherichia coli*
2. *Salmonella dublin*
3. *Clostridium perfringens*, types B and C
4. *Clostridium chauvei*
5. *Haemophilus somnus*
6. *Myxovirus parafluenza* 3
7. Infectious Bovine Rhinotracheitis; and
8. *Salmonella typhimurium*

EIA or equivalent test procedures will typically be configured to assay the presence and concentration of pathogen specific antibodies to this group of common pathogens. The scope of the assay techniques actually implemented in practicing the present invention on a commercial scale will depend on the complexity, repeatability and cost of the selected procedures as well as requirements for enhanced levels of passive immunity to specifically identified pathogens. For example, test procedures may be modified or expanded under certain conditions to determine the distribution and concentration of antibodies specific to pasteurella, clostridium perfringens, type D, Rota virus, Corona virus and others.

The specific assay techniques implemented in practicing the invention on a commercial scale will therefore typically be compatible with the group of pathogen specific antibodies incorporated in the specific quality control standard actually implemented to evaluate the acceptability of identified batches of filtered product. The assay techniques may be modified as necessary to accommodate different quality control standards, for example regionalized quality control standards.

To use the filtered product to control the transfer of passive immunity to the newborn calf, a predetermined quantity of the filtered product is dissolved in a liquid such as colostrum, milk or water to produce a one to two liter Ig solution. This Ig solution is fed to the calf during the critical absorption period, generally within twelve hours and ideally within two hours postpartum. Since a newborn calf typically consumes a maximum of only one to two liters of liquid during the initial suckling, it is desirable that the Ig concentration of the Ig solution is high enough to effect the transfer of an appropriate number of Ig molecules into the calf blood serum to achieve a minimum effective blood serum Ig concentration.

Market studies have indicated a user preference for administering medication to animals in dry form rather than in liquid form. In response to this expressed preference, the filtered product may be manufactured in pellet or capsule form. Packaging the filtered product in a two-section gelatinous capsule involves straight forward, existing technology and avoids exposing the filtered product to heat. After ingestion by the calf, the capsule dissolves and releases the filtered product. The filtered product subsequently dissolves in liquid such as water, milk or maternal colostrum consumed by the calf at the time of medication administration. The Ig from the resulting Ig solution is then absorbed through the calf's gut. Whether administered in dry or liquid form, the filtered product dosage remains the same.

To achieve calf blood serum Ig concentration levels of at least 15 mg/ml and preferably 20 mg/ml taught by the prior art as necessary to achieve an adequate transfer of passive immunity, a liquid Ig solution having a substantially higher Ig concentration must be ingested by a typical one hundred pound neonate calf. Since only about two hundred grams of the filtered product can be dissolved in one liter of colostrum, milk or water and since a neonate calf typically ingests only one to two liters of liquid per feeding, a filtered product having a forty to fifty percent Ig weight concentration should be capable of achieving a calf blood serum Ig concentration level recognized as acceptable by the prior art.

The flexibility of the present invention in controlling the distribution and concentration of pathogen specific antibodies in the filtered product will now be described in detail. When necessary, it may be advantageous to blend two or more different lots of dried immunologically active filtered product to produce a blended product meeting quality control standards which are not met by a single product lot.

By using more complex filtration procedures and ultrafiltration membranes capable of eliminating higher levels of non-Ig molecules, the ultrafiltration process is capable of producing an immunologically active filtered product which has an increased Ig concentration and hence an increased concentration of each pathogen specific antibody. In many cases, the resulting more concentrated filtered product produced by higher levels of ultrafiltration may meet the designated quality control standards where the less concentrated filtered product failed to meet such standards.

Even without implementation of the blending techniques described above, the filtered product produced according to the process of the present invention tends to achieve a comparatively homogeneous distribution and concentration of pathogen specific antibodies since the milk processed into the whey Ig source material is typically drawn from a large, geographically distributed population of cows. While the milk produced by a single cow or by a small herd of cattle may lack necessary or desirable pathogen specific antibodies or may possess low Ig concentrations, the filtered product should not reflect the immunological inadequacies of such limited milk samples. On the contrary, due to its homogeneous nature, the filtered product will possess more uniformly useful immunological properties.

Numerous other different techniques for exercising positive control over the natural passive immunity transfer mechanism are available as a direct result of implementing the process of the present invention to produce a filtered product having a high concentration of immunologically active Ig molecules. Such additional techniques and resulting benefits would be obvious to a person of ordinary skill in the art in view of the teachings recited above.

When the process of the present invention is implemented in a selected manufacturing facility, the feedstock and the intermediate and ultimate products should be assayed by means of the testing techniques described above to verify that Ig immunological activity has been substantially maintained. If at any step in the process the magnitude of the Ig immunological activity is significantly reduced or eliminated, the cause should be identified and corrected. Typically, reduction or elimination of Ig immunological activity is caused by excessive temperatures, exposure to a given temperature for an excessive time, excess microbial activity or molecular damage caused by excessive microbial enzyme activity.

The passive immunity transfer mechanism implemented according to the present invention has been discussed primarily in connection with dairy cattle. However, beef cattle and other non-bovine domestic animals that achieve passive immunity to disease in response to ingestion of a colostrum-like mammary gland secretion can also benefit from implementation of the process of the present invention. Dairy cattle have been focussed upon primarily due to the recognized and publicized immunity problems encountered and the resulting highly adverse economic impact on dairymen.

A recently published research study suggests the possibility that bovine antibodies such as the anti-rotavirus antibody may possess sufficient activity against human rotavirus strains to provide protection against symptomatic infection. If further investigation establishes that bovine antibodies do in fact combat selected human diseases, the immunologically active filtered product of the present invention could be used to provide protection against those diseases in humans.

Results of experiments involving the use of the whey-derived product described above will now be discussed in detail.

EXAMPLE 1

The inventive process described above was implemented by generally following the process steps described above. Clarified whey was processed into a primary product having a thirty-five percent protein concentration with a five percent Ig concentration in a primary ultrafiltration bank incorporating a 10,000 Dalton ultrafiltration membrane. The primary product was then directed to a secondary ultrafiltration bank incorporating a single 100,000 Dalton ultrafiltration membrane. The ultrafiltration equipment and feedstock were maintained at ambient temperature during the filtration process. Repeated filtration with diafiltration was accomplished. This process ultimately yielded dry, powdered secondary product having a seven percent Ig concentration in an approximately eighty percent protein retentate.

Prior art research studies have indicated that the Ig content of colostrum and the quantity of colostrum consumed by a calf shortly postpartum must be sufficient to yield a calf blood serum Ig concentration of at least 15 mg/ml and preferably 20 mg/ml or higher. The seven percent Ig concentration of this filtered product and its maximum Ig concentration when dissolved in milk fell far short of the minimum Ig concentration taught by the prior art as necessary to achieve a transfer of passive immunity in a neonate calf. Nevertheless, this filtered product was tested on a group of dairy calves to investigate whether this whey-derived product had any potential for controlling or regulating the immune system of a neonate calf. The results of this first test of the filtered product are summarized in Table 1 below: t each Group 3 calf received a total of six hundred grams of the filtered product. Since the seven percent Ig concentration of each three hundred gram dose of the product yielded a total of twenty-one grams of Ig per dose, each Group 3 calf received a total of forty-two grams of whey-derived Ig by consuming six hundred grams of the filtered product dissolved in milk.

Calf Group 4 received two two liter feedings of milk in which one hundred grams of filtered product had been dissolved. Each dose included a total of seven grams of Ig and the calf received a total of fourteen grams of whey-derived Ig.

Calf Group 5 received a single dose of one hundred grams of the filtered product dissolved in two liters of milk within about four hours postpartum. This group therefore received only seven grams of whey-derived Ig.

Blood samples were taken from each calf prior to its initial feeding, again twenty-four hours later, and at five, ten and twenty days postpartum. Each blood sam-

TABLE I

| CALF GROUP | Ig SOURCE | DOSAGE | TOTAL Ig INGESTED PER DOSE | TOTAL Ig INGESTED | Ig CONCENTRATION IN LIQUID DOSE | Ig CONCENTRATION IN ANIMAL BLOODSTREAM | 30-DAY MORBIDITY SCORE | LONG TERM HEALTH/ GROWTH RATE |
|---|---|---|---|---|---|---|---|---|
| 1 | Milk | 2 liters, 2 times | Near Zero | Near Zero | Near Zero | Near Zero | 25 | Much worse than Control Group |
| 2 | Colostrum | 2 liters, 2 times | 100–360 g | 200–720 g | 50–180 mg/ml | 17–35 mg/ml | 50 | Control Group |
| 3 | Product (600 g) | 2 liters, 2 times, 300 g Prod per dose | 21 g | 42 g | 10.5 mg/ml | 3–4 mg/ml | 80 | Better Than Control Group |
| 4 | Prodcut (200 g) | 2 liters, 2 times 100 g Prod per dose | 7 g | 14 g | 3.5 mg/ml | 1–1.5 mg/ml | 58 | As Good As Control Group |
| 5 | Product (100 g) | 2 liters, 1 time 100 g Prod | 7 g | 7 g | 3.5 mg/ml | (1 mg/ml) | 33 | Much Worse Than Control Group But Better Than Group 1 |

Thirty neonate calves were collected and divided into five groups of six calves each. One Group 3 calf bled to death because its umbilical cord was clipped too close to its navel. Since the cause of death of the calf was unrelated to the experiment, its death was not reflected in the Group 3 test results.

Special arrangements were made to obtain these calves before they had an opportunity to suckle colostrum from their dams. The Group 1 calves were fed two liters of milk within about four hours postpartum and a second two liter feeding of milk approximately twelve hours after the first feeding. The Group 1 calves were deprived of Ig other than the insignificant levels of Ig normally found in whole milk.

The Group 2 calves served as a control group and received Ig via natural colostrum during their first two feedings postpartum. The timing of the two feedings was the same for all animals used in this initial test.

Calf Groups 3, 4 and 5 received whey-derived Ig via the filtered product produced through use of the 100,000 Dalton ultrafiltration membrane as described above. The Group 3 calves received two separate two liter feedings of milk. Three hundred grams of product was dissolved in each two liter feeding of milk such that ple was assayed for total Ig content and for pathogen-specific antibody activity against six pathogens commonly occurring in calves. The total Ig content was determined by a Radial-Immune-Diffusion (R.I.D.) procedure against goat antibovine immunoglobulin. The enzyme-linked immunoassay (E.I.A.) procedure was used to determine pathogen-specific activity. Two determinations were made, one using goat antibovine immunoglobulin and one using a mouse antibovine immunoglobulin from a monoclonal hybridoma. Antigens for the pathogens tested came from commercial vaccines.

The calves acquired for this experiment were purchased at birth from eight different dairy farms. Eleven calves were obtained from one farm, eight from a second farm and the rest were distributed among the remaining six farms. To the maximum extent possible, all thirty calves used in this experiment received similar handling and treatment.

Four of the six Group 1 calves died within a few days after birth. The difference between the Group 1 milk-treated calves and the other calf groups which received either colostrum or the product was dramatic. The Group 1 calves were apparently not capable of controlling the transport of pathogenic organisms through the intestinal epithelium into systemic circulation. The Group 2-5 calves appeared to adequately limit this unwanted transport of pathogenic organisms.

The blood serum data indicated that two Group 1 calves had attained low Ig concentrations (0.3 and 2.3 mg/ml) prior to the first feeding. This Ig was apparently obtained via placental transfer or by undetected suckling of colostrum and was sufficient to protect these two animals from the transfer of pathogens during the first twenty-four hours of life while the epithelial cells were still capable of transferring ingesta into systemic circulation. In subsequent serum samples, these two resistent calves showed evidence of producing their own antibodies as indicated by increasing amounts of total serum Ig and by pathogen-specific activity. The four Group 1 calves which died failed to show any evidence of increased antibody activity.

The Group 2 or control group calves were fed a maximum amount of high Ig concentration first milking colostrum having high levels of pathogen-specific antibodies of both polyclonal and monoclonal determination. Each calf received colostrum from a different cow, and in most cases, from a diary other than the one where it was born. As expected, the resulting serum Ig concentration in all Group 2 calves at twenty-four hours post-feeding was very high (17-35 mg/ml.).

The Group 3 calves received a total of six hundred grams of the product which included forty-two grams of whey-derived Ig. These calves absorbed sufficient Ig to show a blood serum Ig level of 3-4 mg/ml and significant pathogen-specific antibody activity by twenty-four hours postpartum. The Group 3 calves experienced no mortality and only limited morbidity.

The Group 4 calves received two hundred grams of the filtered product containing fourteen grams of whey-derived Ig. These calves attained blood serum Ig concentration of 1-1.5 mg/ml. In comparison to the Group 3 calves, the Group 4 calves had less pathogen-specific antibody activity at twenty-four hours postpartum, less active antibody and Ig production at twenty days postpartum and a higher level of mortality and morbidity. Two Group 4 calves died five days postpartum due to excessive diarrhea and dehydration.

The Group 5 calves received one hundred grams of the product containing seven grams of Ig. These calves were subject to high levels of morbidity and mortality. The amount of Ig received by these calves was sufficient to prevent septicemia or apparent absorption of ingested pathogenic microorganisms, but they were initially highly subject to diarrhea and subsequently to respiratory disease. Most of the Group 5 calves remained chronically morbid and two died at an early stage as a result of alimentary disease. One Group 5 calf attained a blood serum concentration of 1.2 mg/ml and showed significant pathogen specific antibody activity from twenty-four hours postpartum through twenty days postpartum.

This initial experiment demonstrated that the wellbeing of a calf and its resistance to disease depended upon the absorption of a sufficient quantity of whey-derived Ig to achieve a blood serum concentration of at least one milligram per milliliter or better and the development of pathogen-specific antibodies at twenty-four hours postpartum. Any calves which did not meet these minimal requirements succumbed to disease and were generally chronically morbid.

All thirty of the calves involved in this initial experiment were carefully observed on a daily basis over the entire sixty day duration of the experiment. A combined subjective/objective morbidity score was maintained for each calf. As indicated by Column 7 of Table I, the Group 3 product-fed calf morbidity score of 80 substantially exceeded the Group 2 colostrum-fed calf morbidity score of 50. The morbidity scores of the milk-fed calves and of the Group 5 product fed calves fell substantially below the morbidity score of the Group 2 colostrum-fed calves.

Upon completion of this sixty-day experiment, calf mortality, morbidity and growth were carefully evaluated. The morbidity entries in Table 1 indicate the relative, long term overall performance of each calf group. As indicated, the Group 3 calves which received forty-two grams of whey-derived Ig outperformed the Group 2 colostrum fed calves. This result was surprising and totally unexpected in that the prior art uniformly taught that a sufficient amount of Ig must be consumed to achieve a calf blood serum Ig level of at least 15 mg/ml and preferably 20 mg/ml shortly postpartum to achieve adequate performance of a calf's immune system. In fact, the Group 2 colostrum-fed calves did achieve Ig blood serum levels of 17-35 mg/ml precisely as taught by the prior art and did achieve highly satisfactory immune system performance. Although the Group 3 product-fed calves achieved blood serum Ig levels of only 3-4 mg/ml, levels dramatically below the minimum acceptable levels taught by the prior art, the immune systems of these product-fed calves significantly outperformed the immune systems of the colostrum-fed calves.

In addition, the whey-derived Ig produced according to the process of the present invention satisfactorily accomplished each of the three separate immune system objectives known to be accomplished by natural colostrum. First, natural colostrum must function to prevent pathogenic organisms from entering the systemic circulation of the calf during the critical absorption period discussed above. During this critical absorption period, the neonate calf is capable of transferring Ig and other ingesta through the epithelial cells lining the intestinal wall into systemic circulation. As described above, only the Group 1 milk-fed calves showed symptoms and died of septicemia, indicating a total failure to achieve this first immune system performance objective. As indicated by the experimental test results tabulated in Table I, the whey-derived product, even at low Ig concentrations, was as effective as high Ig concentration natural colostrum in controlling pathogenic organism transfer via the small intestine during the critical absorption period. This experiment therefore confirmed that the whey-derived product did accomplish this first immune system performance objective. d The second immune system performance objective relates to the provision of an adequate level of Ig for intestinal absorption during the critical absorption period to provide effective passive immunity to the neonate until its active immunity becomes effective. The total quantity of whey-derived Ig fed to the Group 3-5 calves was only a fraction of the 200-720 gram Ig doses consumed by the Group 2 colostrum fed calves. Nevertheless, the Group 3 calves which received only forty-two grams of Ig attained a blood serum Ig concentration of 3-4 mg/ml which resulted in an eight to tenfold increase in pathogen specific antibody activity in all six pathogens evaluated in this experiment. Furthermore, the Group 3 calves experienced a zero mortality rate and a morbidity score of eighty in comparison to the morbidity score of fifty of the Group 2 colostrum-fed calves. The Group 4 calves received only fourteen grams of whey-derived Ig yet experienced only two deaths and limited morbidity of the survivors—a level of immune system performance comparable to or better than the surviving Group 2 colostrum-fed calves.

The third immune system performance objective relates to the initiation of the calf's active immune system. A neonate calf relies on its Ig-derived passive immunity until its active immune system is activated and is able to produce an adequate, sustained level of antibody activity. Effective passive immunity enhances the ability of neonates to develop active immune responses thus affecting long term as well as short term health. If neonates consuming the whey-derived product did not achieve optimal active immune system function, the product could not function as a substitute for natural colostrum. The measurements made in connection with the Example 1 experiment clearly demonstrated that the four Group 1 calves which did not receive either placental or colostral Ig transfer did not show any increase in pathogen-specific activity from birth until death while both the colostrum fed calves and the product-fed calves did initiate the active immune system.

The Example 1 experiment demonstrates that the Group 3 calves which received forty-two grams of the whey-derived Ig achieved overall immune system performance superior to that achieved by the Group 2 calves which received two maximum volume doses of high Ig concentration natural colostrum. The concentration of antibodies to the six pathogens measured in the colostrum-fed calves substantially exceeded corresponding concentrations in any of the product-fed calves. The superior immune system performances of the Group 3 product-fed calves therefore tends to suggest that the whey-derived product contained antibodies for a much greater number of pathogens than were present in the colostrum taken from individual cows. The fact that the whey-derived Ig was derived from pooled milk representing literally hundreds of cows could readily explain the presence of a substantially broader spectrum of antibodies in the whey-derived product than with natural colostrum. This potential for securing broad spectrum immunity from whey-derived product represents a substantial advantage of the product over natural colostrum and provides a method for regulating both the level of activity of a calf's immune system as well as a method for controlling the spectrum of pathogens which can be effectively neutralized by a calf's immune system. The Example 1 experiment therefore establishes that the whey-derived product is capable of functioning as a fully acceptable substitute for natural colostrum 1) by preventing pathogenic organisms from entering systemic circulation during the neonatal stage, 2) by transferring effective passive immunity comparable to or better than natural colostrum and 3) by providing factors which initiate and enhance broad spectrum active immunity at an early stage.

EXAMPLE 2

The whey-derived filtered product was tested a second time with five separate groups of ten calves each as indicated by Table II below. A 120,000 Dalton spiral ultrafiltration membrane and a 100,000 Dalton hollow fiber ultrafiltration membrane were used independently in a secondary ultrafiltration bank to produce separate batches of a secondary product having a nine percent Ig concentration. Techniques essentially identical to those used in connection with Example 1 were utilized to produce these two batches of filtered product. The Group 1 colostrum-fed calves were used as a control group in a manner similar to that discussed in connection with the Group 2 calves of Example 1. The feedings of all calves in the Example 2 experiment were accomplished within four hours postpartum and again twelve hours later. This test was conducted under highly severe weather conditions with calf exposure to an unusually broad spectrum of pathogens.

TABLE II

| CALF | Ig SOURCE | DOSAGE | TOTAL Ig INGESTED PER DOSE | TOTAL Ig INGESTED | Ig CONCENTRATION IN LIQUID DOSE | LONG TERM HEALTH |
|---|---|---|---|---|---|---|
| 1 | Colostrum | 2 liters, 2 times | 100–360 g | 200–720 g | 50–180 mg/ml | Control Group |
| 2 | Product Spiral 300 g | 2 liters, 2 times 150 g Prod. per dose | 13.5 g | 27 g | 6.75 mg/ml | Much Worse Than Control Group |
| 3 | Prodcut Spiral 300 g | 1 liter 1 time 300 g Prod. 2 liters, 1 time, colostrum | 27 g via Product Plus Colostrum | 27 g via Product Plus Colostrum | 13.5 mg/ml | Worse Than Control Group |
| 4 | Product Spiral 600 g | 2 liters, 2 times 300 g Prod per dose | 27 g | 54 g | 13.5 mg/ml | Worse Than Control Group |
| 5 | Product Hollow Fiber 600 g | 2 liters, 2 times 300 g Prod per dose | 27 g | 54 g | 13.5 mg/ml | As Good As Control Group |

The Group 2 calves were administered two one hundred fifty gram doses of the product dissolved in the milk for a total transfer of twenty-seven grams of whey-derived Ig. As indicated by the last column of Table II, the Group 2 calf immune system performance was much worse than that of the Group 1 control group.

Within four hours postpartum, the Group 3 calves were administered three hundred grams of the product dissolved in milk for a total transfer of twenty-seven grams of whey-derived Ig. The second feeding took the form of a two liter dose of natural colostrum including between two hundred to seven hundred and twenty grams of colostrum-derived Ig. The immune system of the Group 3 calves responded well during the early stages of this experiment, but ultimately produced calves having long term health worse than that of the control group.

The Group 4 calves were administered two three hundred gram doses of the product dissolved in milk for a total transfer of fifty-four grams of whey-derived Ig. The immune system of the Group 4 calves performed very well and produced calves having long term health somewhat worse than that of the control group.

The Group 5 calves were administered two three hundred gram doses of the product dissolved in milk for a total transfer of fifty-four grams of whey-derived Ig. The immune system of the Group 5 calves performed very well and produced calves having long term health as good as that of the control group.

The results of this second experiment parallel the results of the first experiment. The Table II data indicates that under extremely severe conditions, fifty-four grams of whey-derived Ig is capable of producing a highly satisfactory immune system performance. The superior immune system performance achieved by the Group 5 calves which received fifty-four grams of whey-derived Ig is consistent with the superior immune system performance achieved by the Group 3 calves of the first experiment which received forty-two grams of whey-derived Ig.

The inferior immune system performance achieved by the Group 2 calves indicates that the administration of only 13.5 grams of whey-derived Ig at each of the two initial feedings did not achieve a performance level which would render this Ig dosage acceptable as a substitute for natural colostrum. Although the immune system of the Group 3 calves that received twenty-seven grams of the product followed by colostrum performed worse than the control group under the severe conditions of this test, such performance indicates that a twenty-seven gram dosage may be adequate under more normal conditions.

EXAMPLE 3

The whey-derived product of the present invention was tested a third time at a second facility separate from the one used to accomplish the Example 1 and Example 2 experiments. This third test involved a total of sixty calves from a single herd which were divided into three groups of twenty calves each. This test was conducted under highly favorable test conditions.

Two different concentrations of Ig were used in implementing this third experiment. A secondary ultrafiltration bank having a 100,000 Dalton hollow fiber ultrafiltration membrane was used to process a thirty-five percent protein primary product into a secondary product having a nine percent Ig concentration. Longer duration processing of the primary product within the same secondary ultrafiltration bank produced a secondary product having a twelve percent Ig concentration. Calves were fed either three hundred grams of the nine percent Ig concentration product or two hundred twenty-seven grams of the twelve percent Ig concentration product dissolved in one liter of milk in order to transfer a total of twenty-seven grams of whey-derived Ig via a single dose. The results of this experiment are tabulated in Table III below.

TABLE III

| CALF GROUP | Ig SOURCE | DOSAGE | TOTAL Ig INGESTED VIA PRODUCT | LONG TERM HEALTH |
| --- | --- | --- | --- | --- |
| 1 | Colostrum | 5 × 1 liter Feedings Thru Day 4 | — | Control Group |
| 2 | Product | 1 liter, 1 time 300 g 9% Ig Prod or 227 g 12% Ig Prod. | 27 g | As Good As Control Group |
| 3 | Product Followed by Colostrum | 1 liter Prod 1 time (300 g 9% or 227 g 12%) - Then, 4 × 1 liter Feedings of Colostrum Thru Day 4 | 27 g | As Good As Control Group |

The Group 1 calves received five separate one liter feedings of natural colostrum through the fourth day postpartum. This group served as the control group. The Group 2 calves received twenty-seven grams of whey-derived Ig dissolved in one liter of milk. The last column of Table 3 indicates that the immune system of the Group 2 calves functioned to achieve long term health as good as that of the control group.

The Group 3 calves received twenty-seven grams of whey-derived Ig dissolved in one liter of milk at the initial postpartum feeding. This group then received four additional one liter feedings of natural colostrum through the fourth day postpartum. The immune system of the Group 3 calves functioned to achieve long term health as good as that of the control group.

This third experiment indicated that if twenty-seven grams of the whey-derived Ig product are administered shortly postpartum, an immune system performance comparable to that attainable by natural colostrum may be achieved under good conditions. This result when contrasted with the result achieved by the Group 2 calves in the Example 2 experiment indicates that under good conditions twenty-seven grams of whey-derived Ig represents a therapeutically effective dosage of Ig which achieves each of the three objectives achieved by natural colostrum. This is consistent with the results obtained under severe conditions by the Group 3 calves in the Example 2 experiment and indicates that a second feeding dose of natural colostrum may not be essential to achieve an adequate level of immune system performance. The fact that the Group 4 calves in the Example 1 experiment received only fourteen grams of whey-derived Ig and that this level of Ig achieved immune system performance comparable to that attainable through use of natural colostrum tends to indicate that whey-derived Ig produced according to the process of the present invention should be administered at a level of at least about fourteen grams. A minimum level of whey-derived Ig of about fourteen grams, desirably at least about twenty-seven grams, therefore appears to represent a therapeutically effective dosage capable of achieving immune system performance comparable to that attainable through use of natural colostrum under good conditions. To achieve immune system performance under severe conditions equal to or better than that available from use of high quality natural colostrum, a therapeutically effective dosage of approximately 40-50 grams of Ig should be ingested by the neonate during the first twelve hours postpartum.

Although the experimental test results recited in Tables I, II and III have expressed the quantity of Ig ingested by a calf in terms of grams, the ratio of the weight of the whey-derived Ig to animal weight is the appropriate parameter to evaluate in determining a therapeutically effective dosage of the product for any particular animal. Since substantially all of the animals used in the various experiments described above weighed from between ninety to one hundred pounds, animal weight was not a significant variable and was disregarded in tabulating these results.

If the experimental results are evaluated as indicating that a therapeutically effective minimum dosage of twenty-five grams or an optimum therapeutically effective dosage level of forty to fifty grams of whey-derived Ig should be administered to a calf having a weight of one hundred pounds, these results indicate that at least a minimum 0.055 and preferably 0.09-0.10 percent ratio of whey-derived Ig to animal weight should be administered to any neonate calf. Applying this ratio to a neonate calf having a body weight of one hundred and twenty-five pounds (56,750 grams) indicates that a minimum of appropriately thirty-one grams of whey-derived Ig should be administered to that calf in a single dose given within four hours postpartum. Various other product dosage levels, dosage distributions and dosage combinations with natural colostrum would be readily apparent to one of ordinary skill in the art in view of the detailed experimental results tabulated above. Therapeutically effective dosages for animals other than calves to yield immune system performance comparable to that of natural colostrum may be determined by testing of the type described above in connection with Examples 1, 2 and 3.

It is clear that the whey-derived product of the invention could readily function as a supplement for natural colostrum to either boost the effective level of Ig in natural colostrum having an insufficient level of Ig or to serve as a source of broad spectrum active immunity ultimately achieved by the immune system of a calf or other bovine. The whey-derived product could also be used on a continuous basis as a food supplement for a calf, a mature cow or any other animal including humans to enable the immunologically active immunoglobulin and other immunologically active whey components in the product to attack pathogens present in the animal digestive system. Comparatively low levels of the product could be used when it functions as a food supplement, potentially on the order of approximately two grams or less per day per hundred pounds of animal weight.

To test this hypothesis, a thirty-eight animal sixty day test was accomplished. Nineteen feeder calves (about three hundred pounds body weight) served as a control group and received normal high protein feed rations. The remaining nineteen feeder calves consumed normal high protein feed rations plus a supplement of approximately five to ten grams per day of filtered product having a seven percent Ig concentration.

During the first thirty days of this test, the daily weight gain of the product-fed calves exceeded the control group daily weight gain by 0.4 pounds—a sixteen percent higher average daily weight gain. During the second thirty days of the test, the daily weight gain of the product-fed calves exceeded the control group daily weight gain by 0.3 pounds per day. In general, the product-fed calves appeared healthier and experienced a higher growth rate and lower morbidity than the control group calves. This test appeared to prove the utility of the whey-derived product as a feed supplement for either growing or mature animals.

A quantity of whey-derived filtered product was produced using a secondary ultrafiltration bank including a 100,000 Dalton hollow fiber ultrafiltration membrane as described above in connection with Example 3. Recirculation and diafiltration techniques were used in an attempt to obtain a maximum Ig concentration. This experiment ultimately yielded a filtered product having a twelve percent Ig concentration.

Figure 2:
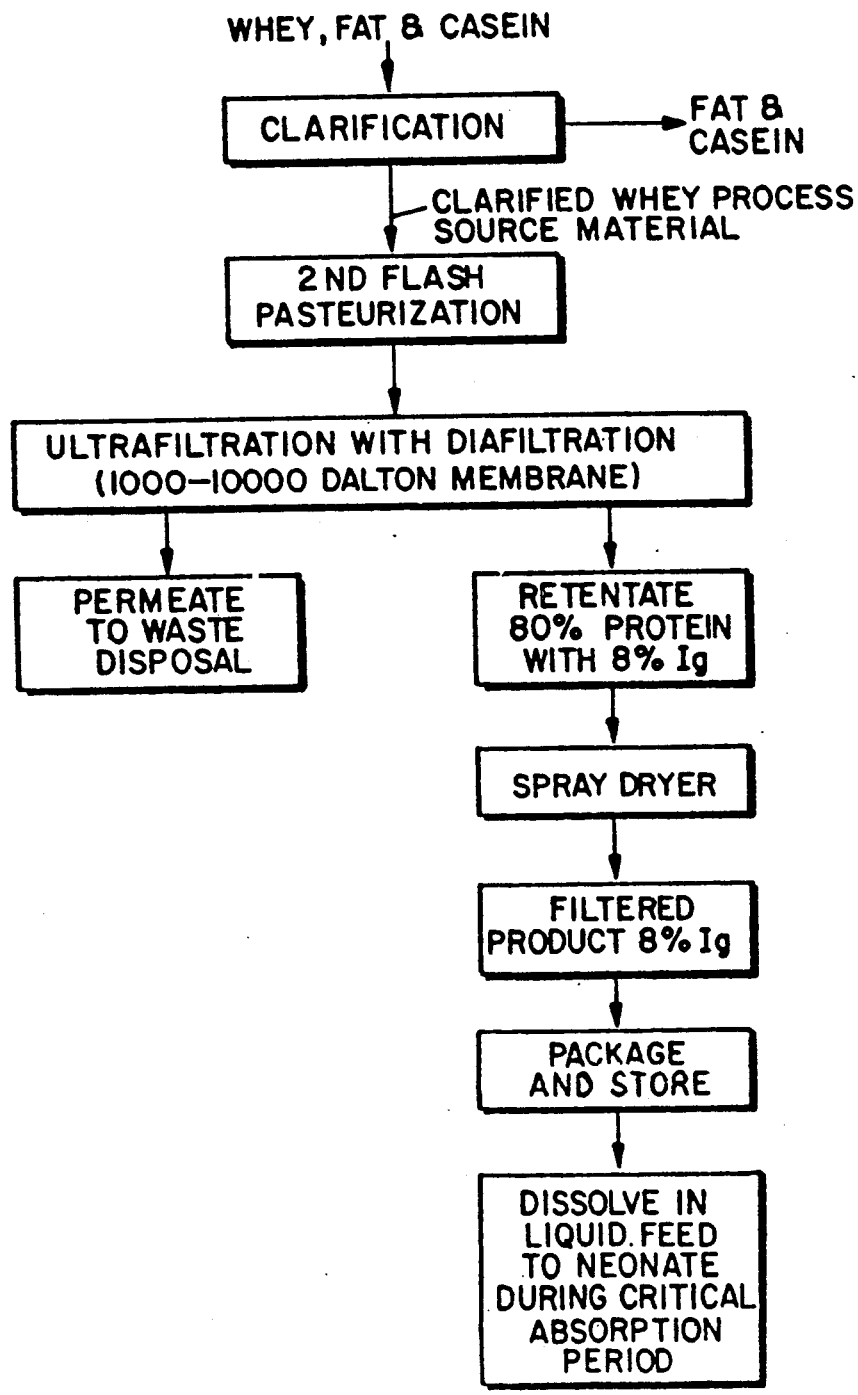
FIG. 2 is a process flow diagram illustrating a revised ultrafiltration process for producing high Ig concentration filtered product.

Referring now to FIG. 2, an ultrafiltration system slightly modified from that described above will be described in detail. The whey, fat and casein feedstock is clarified in a standard item of cheese processing equipment to produce a fat and casein byproduct and a clarified whey source material used in practicing the present invention. The clarified whey is then directed through pasteurization equipment to accomplish a second flash pasteurization which destroys unwanted bacteria remaining in the whey as a result of the utilization of lactobacillus bacteria and rennet as agents in the cheese manufacturing process. This second short duration flash pasteurization has been implemented and found to have no adverse effects on the immunological activity of the Ig molecules in the clarified whey.

The pasteurized whey is then directed to ultrafiltration equipment which incorporates one or more ultrafiltration membranes having permeability levels of from 1,000 to 10,000 Daltons. Experience with the 100,000 Dalton ultrafiltration membrane described above has indicated that a gel rapidly forms on the ultrafiltration membrane substantially reducing its permeability to a level well below 100,000 Daltons. An ultrafiltration membrane having a permeability of from 1,000 to 10,000 Daltons adequately eliminates the unwanted water, lactose and minerals from the whey. The residual level of lactose and minerals in the ultrafiltration retentate does not produce unwanted side effects when the whey retentate is dried and administered to neonate calves.

The ultrafiltration permeate is directed to a waste disposal unit. The ultrafiltration retentate includes approximately eighty percent protein material having an Ig concentration on the order of eight percent. This retentate is directed to a spray dryer which yields a dry, filtered product having approximately an eight percent Ig concentration which has been tested and proven to have substantial immunological activity. This whey-derived filtered product is then packaged and stored and is ultimately dissolved in a liquid such as milk or water and fed to a neonate during the critical absorption period as described above. This whey-derived Ig will possess a broad spectrum of antibodies since it is derived from the whey byproduct of milk obtained from hundreds of cows in geographically distributed, separate herds.

The ultrafiltration processes described initially and in connection with FIG. 2 are capable of producing a colostrum substitute filtered product which can be manufactured and sold at a profit. However, to enhance the profitability of the product incorporating whey-derived Ig, it is desirable to reduce the size of the dose to a level substantially below the six hundred gram dosage level administered to the Example 1 Group 3 calves. Since about eighty percent of the dry filtered product obtained from the ultrafiltration process represents proteins which have a high economic value as a food product, it would substantially enhance the economic attractiveness of the process if some non-Ig protein components in the dry filtered product could be eliminated from the product to increase the Ig concentration in the product. If this could be accomplished, such non-Ig proteins could be sold as a food product through existing commercial channels and could thereby reduce the net cost of manufacturing the product administered to neonate calves in practicing the present invention.

Figure 3:
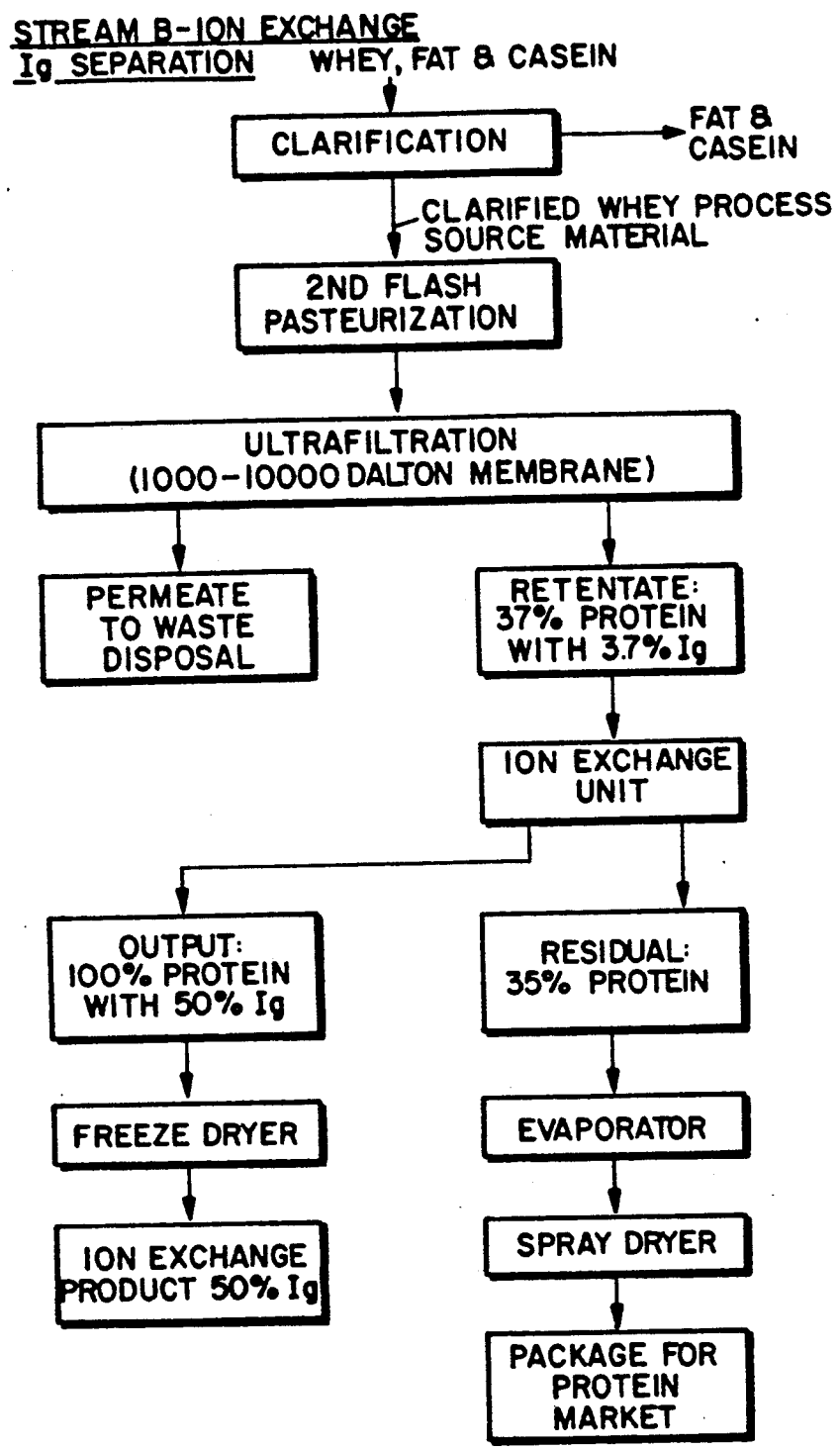
FIG. 3 is a process flow diagram illustrating a combined ultrafiltration/ion exchange process for separating immunologically active Ig molecules from whey.
Figure 4:
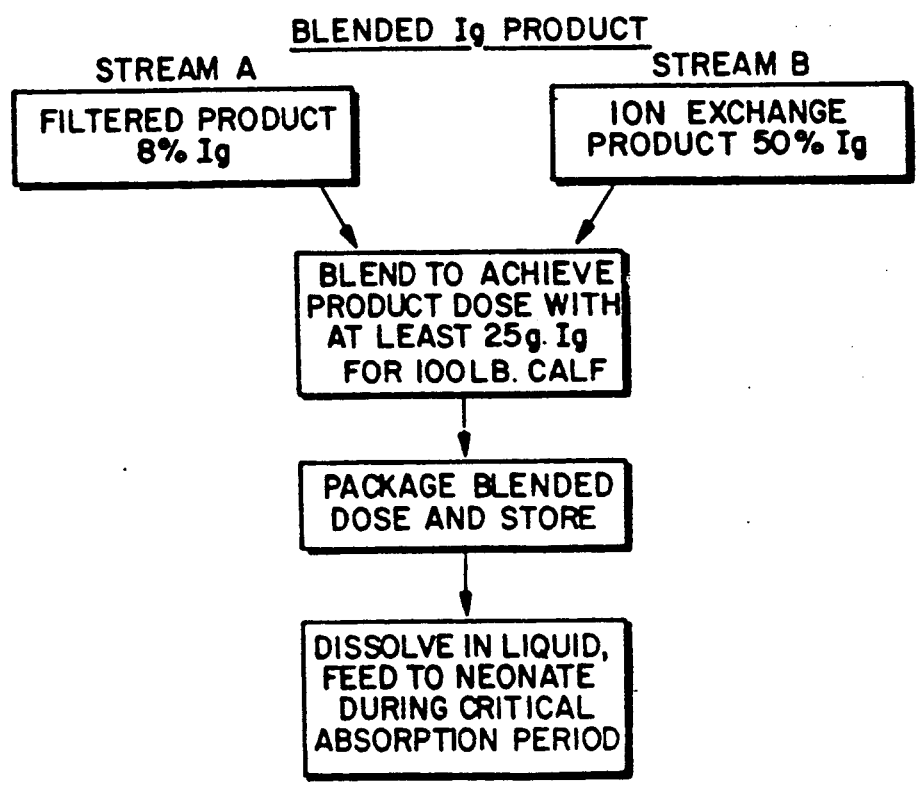
FIG. 4 is a process flow diagram illustrating the manner in which filtered product from the Stream A process depicted in FIG. 2 is combined with highly concentrated Ig material from the Stream B ion exchange unit depicted in FIG. 3 to produce a blended product having an Ig concentration level substantially above levels achievable through use of ultrafiltration alone.
Figure 5:
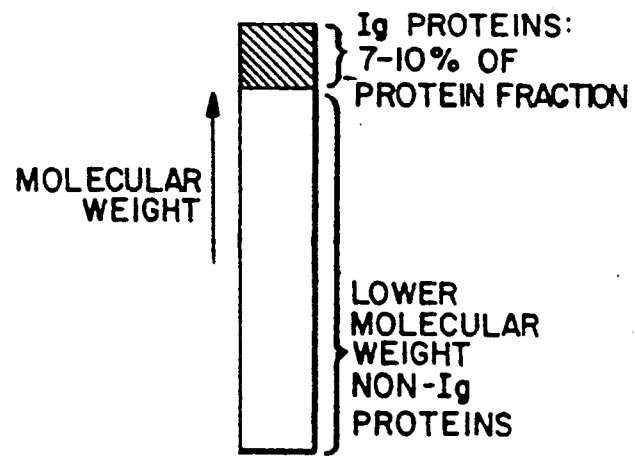
FIG. 5 illustrates the composition of the whey protein fraction.

Referring now to FIGS. 2, 3 and 4, the output of an ultrafiltration system can be combined with an ultrafiltration/ion exchange system to produce, a blended product having a substantially enhanced Ig concentration without a significant reduction in the concentration of smaller molecular weight proteins. With such an enhanced Ig concentration in the blended product, an adequate level of whey-derived Ig can be transferred in a significantly reduced product dose size resulting in a substantial cost savings by avoiding the use of a significant percentage of the non-immunologically active protein material.

In implementing this different technique for producing a colostrum substitute product, the FIG. 2 ultrafiltration process is utilized to produce a filtered product having approximately an eight percent Ig concentration. As indicated in FIG. 4, this Stream A eight percent Ig product is blended with a Stream B ion exchange product having a fifty percent Ig concentration to achieve a significantly higher Ig concentration whey-derived Ig product.

Referring now to FIG. 3, the Stream B combined ultrafiltration/ion exchange process for producing a fifty percent Ig concentration product will now be described in detail. The FIG. 3 process utilizes the same whey, fat and casein feedstock as that used in the FIG. 2 ultrafiltration system. The ion exchange Ig separation as depicted in FIG. 3 may either be accomplished at the same site where the FIG. 2 ultrafiltration system is located or more typically will be performed at a different cheese processing plant.

The feedstock is clarified to remove fat and casein and the clarified whey process source material is directed through a second flash pasteurization step as was the case with the FIG. 2 ultrafiltration system.

Ultrafiltration of the clarified whey is accomplished with an ultrafiltration unit having a 1,000 to 10,000 Dalton ultrafiltration membrane to produce a thirty-seven percent protein retentate. The ultrafiltration permeate is directed to a waste disposal unit. Diafiltration may be used with this ultrafiltration process to remove salts from the ultrafiltration retentate such that its conductivity is reduced to a near zero level on the order of 2-3 mMhos. Above such conductivity levels, ion exchange equipment is rendered ineffective. Alternative techniques such as electrodialysis may be used to desalinize the retentate.

The thirty-seven percent protein retentate is then directed to an ion exchange unit of a type well known to those of ordinary skill in the appropriate field. Such an ion exchange unit can be configured to function in either a cation or anion extraction mode. At present, the cation mode is preferred primarily for economic reasons.

The ion exchange unit operates on the whey protein ultrafiltration retentate to separate out Ig proteins possessing a charge different from most non-Ig proteins. When operated as a cation ion exchange system at a pH somewhat lower than the normal 6.2 pH of whey, the bed of the ion exchange unit collects Ig proteins and other proteins at a ratio of approximately fifty percent Ig proteins to fifty percent other proteins. When the bed of the ion exchange unit is eluted, an ion exchange product having about a fifty percent Ig concentration and a fifty percent non-Ig protein concentration is obtained.

When the ion exchange unit is operated in the anion mode at the normal 6.2 pH of whey, the non-Ig proteins bind to the ion exchange bed while the oppositely charged Ig proteins pass through without binding. The anion process also produces about a fifty percent Ig concentration product.

Specific configurations of both cation and anion ion exchange units are recited in Examples 4 and 5 below:

EXAMPLE 4

Ig is purified by a cation exchange using a cation exchange material such as S-Sepharose (Pharmacia) equilibrated with 10 mM acetate, pH 4.5-6.0, e.g. 5.0. A desalted solution of whey proteins with a conductivity of 2 mMhos (2 mS) is adjusted to pH 5.0 and exposed to the S-Sepharos gel at about 2-500 mg/ml of gel, for example 4 ml whey protein solution at 50 mg/ml mixed with 2 ml gel or passed through a column of 2 ml gel. About fifty percent or more of the Ig in the whey protein solution binds to the gel. Unbound proteins are washed away with 10 mM acetate, pH 5.0 or with water (5 ml for 2 ml gel). Ig is released and obtained by exposing the gel to high salt (100 mM NaCl in 10 mM acetate) or high pH (8.0), for example 100 mM dibasic phosphate or ammonium carbonate. Five milliliters eluting buffer is adequate for 2 ml gel.

EXAMPLE 5

Anion exchange is used to purify Ig by binding non-Ig proteins. Anion exchange gel such as Q-Sepharose or Amicon-AM gel is equilibrated with 10 mM phosphate at pH 7.5. A low salt (2 mS) solution of whey proteins is adjusted to pH 7.5 and mixed with anion exchange gel (100 mg protein per ml gel). Unbound protein is collected and is Ig rich (80% or more of the protein is Ig).

Referring now to FIG. 4, the eight percent Ig product obtained via the FIG. 2 process Stream A is blended with fifty percent Ig concentration ion exchange product produced by the FIG. 3 Stream B ion exchange Ig separation process. When the Stream A eight percent product is blended in an appropriate ratio with the Stream B fifty percent Ig concentration product, a product having a controllable Ig concentration of between eight percent to fifty percent Ig may be obtained.

Present economic considerations suggest the desirability of using a product dose of no more than three hundred grams to minimize the cost of the non-Ig protein components.

The experimental test results tabulated above indicate that a high level of immune system performance will be achieved with a single dose of the product containing about forty grams of immunologically active, whey-derived Ig. If two hundred and thirty-eight grams of the Stream A eight percent concentration Ig product (8% × 238 g = 19 g Ig) is blended with forty-two grams of fifty percent concentration Ig from Stream B (50% × 42 g = 21 g Ig), a two hundred and eighty gram dose is produced having forty grams of whey-derived Ig. Forty grams of Ig in a total dose size of two hundred eighty grams represents a fourteen percent Ig concentration.

Since the Stream A ultrafiltration product was filtered only to an eight percent Ig concentration, essentially none of the non-Ig proteins were eliminated from this two hundred thirty-eight gram component of the overall two hundred eighty gram dose. Since the Stream A ultrafiltration retentate was only processed to a maximum protein concentration of eighty percent protein, approximately twenty percent of the retentate will comprise lactose and minerals. Experimental testing has indicated that this comparatively small level of lactose and minerals does not adversely affect neonate calves and will not cause unwanted scours.

As indicated by FIG. 3, the residual product obtained from the second output of the ion exchange unit comprises approximately thirty-five percent protein. This specific percent concentration protein has been selected since this is the standard, commercially acceptable protein concentration for use in the food product market. This thirty-five percent protein product is passed through an evaporator and spray dryer and is ultimately packaged for resale in the existing protein food product market.

The sale of this non-immunologically active protein product provides a substantial process cost recovery and significantly reduces the net cost of the blended, highly concentrated Ig product achieved by combining the Stream A low concentration Ig product with the Stream B high Ig concentration product.

The blended whey-derived product is packaged and marketed. To administer this packaged product to a neonate calf, the package is emptied into an appropriate one or two liter quantity of milk, dissolved and fed to the neonate as described above.

Based on the experimental test results tabulated above, the blended product should contain at least about twenty-five grams of Ig for use as a colostrum substitute with a typical one hundred pound neonate calf under good conditions. The 0.055 percent ratio of Ig weight to animal body weight should be observed for neonate animals having weights differing from the one hundred pound typical neonate calf weight. To achieve immune system performance equal to or better than high quality natural colostrum, approximately forty to fifty grams of Ig should be ingested by the neonate during the first twelve hours postpartum (0.09%–0.10%).

As was the case with the straight ultrafiltration product, the blended Ig product may also be used as a colostrum supplement rather than as a colostrum substitute. In addition, the blended product may be used as an immunologically active food supplement. Although a specific ratio of Stream A product to Stream B product was described above, it would be readily apparent based upon the detailed description above that various other ratios of Stream A to Stream B could be blended together to achieve differing levels of Ig in the blended product. The specific application of the blended Ig product as well as various economic and cost factors would dictate the specific quantity of Stream A which is blended with Stream B.

To compare the immune system performance of calves fed a normal quantity of natural colostrum with that of calves fed comparatively minimal quantities of the whey-derived product of the present invention, a comprehensive investigation of the immunological characteristics of the colostrum and product input materials and of the calf blood serum was conducted. A key objective of these tests was to identify and quantify specific immunologically active components of the whey-derived product responsible for the test results recited in Tables I–III above.

Table IV compares the Elisa assay data for certain pathogen specific antibodies present in the Example 1 secondary product with the Example 1 colostrum and milk input materials. Table IV demonstrates that while ordinary milk possessed comparatively insignificant levels of pathogen specific antibodies in comparison to colostrum, the secondary product possessed pathogen specific antibody levels which exceeded comparable colostrum levels by a factor of from two to twenty times. The Table IV data therefore confirms the substantially enhanced potency of the immunologically active components of the whey-derived product in comparison to natural colostrum.

TABLE IV

| EXAMPLE 1 - INPUT MATERIAL ANTIBODY TITERS | | | |
|---|---|---|---|
| ORGANISM | SECONDARY PRODUCT | COLOSTRUM | MILK |
| IBR | 400 | 200 | <10 |
| B. abortus | 4000 | 200 | 12 |
| Cl. perfringens | 5500 | 350 | 32 |
| E. coli | 4000 | 1250 | 60 |
| H. somnus | 3200 | 180 | 24 |
| S. dublin | 2300 | 450 | 16 |

Table V lists the Example 1 average Elisa calf blood serum antibody titers for the Group 1 milk fed calves, the Group 2 colostrum fed calves and the Group 3 product fed calves at both five and ten days postpartum.

TABLE V

| | EXAMPLE 1 - CALF BLOOD SERUM ANTIBODY TITERS | | | | | |
|---|---|---|---|---|---|---|
| | EIA - 5 DAYS | | | EIA - 10 DAYS | | |
| ORGANISM | GROUP 1 Milk Fed | GROUP 2 Colostrum Fed | GROUP 3 Product Fed | GROUP 1 Milk Fed | GROUP 2 Colostrum Fed | GROUP 3 Product Fed |
| IBR | <5 | 16 | 15 | <5 | 5 | 16 |
| B. abortus | <5 | 80 | 16 | <5 | 20 | 21 |
| Cl. perfringens | <5 | 95 | 34 | <5 | 5 | 30 |
| E. coli | <5 | 230 | 52 | <5 | 23 | 60 |
| H. somnus | <5 | 40 | 60 | <5 | 5 | 16 |
| S. dublin | <5 | 270 | 76 | <5 | 20 | 30 |

Table V demonstrates that the immune system of the Group 1 milk fed calves was essentially inactive at both five and ten days postpartum. The blood serum antibody titers of the Group 2 colostrum fed calves at five days postpartum showed significant antibody levels which by ten days postpartum had substantially decreased in magnitude primarily due to a depletion of the immunologically active components derived from colostrum. Although the blood serum antibody titers of the Group 3 product fed calves were equal to or less than the titers of the Group 2 colostrum fed calves at five days postpartum, by ten days postpartum the blood serum antibody titers of the Group 3 product fed calves substantially exceeded the antibody titers of the Group 2 colostrum fed calves. Table V therefore demonstrates the superior capability of the whey-derived product of the present invention to activate the immune system of neonate calves. The specific immunologically active components responsible for the superior immune system performance evidenced in Table V have not been fully identified at the present time.

Although the level of Ig contained in the secondary product used in connection with the Example 1, 2 and 3 experiments described above was substantially less than the Ig level in average quality natural colostrum, the calf immune system performance achieved by comparatively low dosage levels of the secondary product achieved immune system performance equal to or greater than that achieved by natural colostrum. In order to explain this unusual phenomenon, other potential immune enhancing components of the product were investigated. Raw whey is known to contain immunologically active lactoferrin having a molecular weight of 90,000 Daltons. Besides having a known direct antimicrobial effect, lactoferrin has the capability of complexing with Ig molecules to form an Ig/lactoferrin complex. An Ig/lactoferrin complex was isolated from raw whey and evidenced a molecular weight of about 400,000. A monoclonal antibody specific for this complexed protein molecule was developed and used in a standard EIA test to determine the concentration of the Ig/lactoferrin complex in milk, colostrum and filtered product. The results of this analysis are presented in Table VI.

TABLE VI

EXAMPLE 1 - INPUT MATERIAL Ig/LACTOFERRIN COMPLEX ANTIBODY TITERS

| | EIA TITERS | | |
|---|---|---|---|
| ORGANISM | SECONDARY PRODUCT | COLOSTRUM | MILK |
| IBR | 500 | <100 | <5 |
| B. abortus | 8000 | <100 | <5 |
| Cl. perfringens | 8000 | <100 | <5 |
| E. coli | 8000 | <100 | <5 |
| H. somnus | 6000 | <100 | <5 |
| S. dublin | 7000 | <100 | <5 |

Table VI therefore demonstrates that the Ig/lactoferrin complex has only a negligible activity in milk, only a minimal activity in colostrum, but a substantial activity in the whey-derived product. It is evident that the presence and activity of the high molecular weight Ig/lactoferrin complex in the product contributes to its unexpectedly potent immunological activity.

To identify the mechanism responsible for creating the Ig/lactoferrin complex, the antibody titers of this complex were analyzed both for the raw milk input material and for the milk-derived whey produced during the cheese making process. The results of this analysis are depicted in Table VII. The input material evaluated represented either maternal milk sampled at one, two, five or ten days postpartum or whey derived from those same milk samples. A monoclonal antibody with specificity for the Ig/lactoferrin complex was used in an EIA test to quantify the concentration of this complex. The results of this study are depicted in Table VII.

TABLE - VII

MILK VS. WHEY - Ig/LACTOFERRIN COMPLEX ANTIBODY TITERS

| | MILK | | | | MILK-DERIVED WHEY | | | |
|---|---|---|---|---|---|---|---|---|
| | DAYS POSTPARTUM | | | | | | | |
| ORGANISM | 1* | 2 | 5 | 10 | 1* | 2 | 5 | 10 |
| IBR | <100 | <100 | <10 | <10 | <100 | <100 | 270 | 270 |
| B. abortus | 200 | 200 | 10 | <10 | 1600 | 400 | 270 | 270 |
| Cl. perfringens | 400 | 200 | 10 | <10 | 1600 | 400 | 270 | 270 |
| E. coli | 1600 | 800 | 90 | 30 | 1600 | 400 | 270 | 270 |
| H. somnus | 200 | 200 | 30 | 10 | 1600 | 400 | 270 | 270 |
| S. dublin | 800 | 400 | 30 | 10 | 1600 | 400 | 270 | 270 |

\* = Day 1 Colostrum

By ten days postpartum, the maternal milk sample possessed only minimal levels of the Ig/lactoferrin complex, while the milk-derived whey sample demonstrated both long lasting and substantial levels of this complex. The Table VII data therefore indicates that the Ig/lactoferrin protein complex contributes significantly to the immunological activity of the filtered product of the present invention.

Although not specifically investigated, the following immunologically active components of whey are also present in the fractions included in the filtered product: lysozyme, lactoperoxidase, xanthine oxidase, lymphokines, and mitogens, all of which have molecular weights enabling them to be retained in the ultrafiltration retentate. The immunologically active lactoperoxidase whey protein has been detected in the retentate in low, but significant amounts.

The blood serum Ig levels of the Example 3 calves were tracked until seventy days postpartum. The Ig levels for the Group 1 colostrum fed calves, the Group 2 product fed calves and the Group 3 product plus colostrum fed calves are depicted in Table VIII.

TABLE VIII

EXAMPLE 3 - CALF POSTPARTUM BLOOD SERUM Ig LEVEL

| CALF GROUP | INPUT MATERIAL | DAYS POSTPARTUM | | | | |
|---|---|---|---|---|---|---|
| | | BIRTH | 1 | 15 | 35 | 70 |
| 1 | Colostrum | 0.06 | 19.5 | 14.0 | 16.3 | 22.4 |
| 2 | Product | 0.08 | 1.4 | 2.1 | 11.3 | 22.4 |
| 3 | Product + colostrum | 0.08 | 1.7 | 4.7 | 13.1 | 24.8 |

Although the Ig levels of the Group 2 and 3 product fed calves fell significantly below the Ig levels of the Group 1 colostrum fed calves through thirty-five days postpartum, by 70 days postpartum, the Ig levels of the product fed calves equalled or exceeded the Ig levels of the Group 1 colostrum fed calves. The Table VIII test results therefore establish that a dose of filtered product including twenty-seven grams of immunologically active Ig effects an adequate transfer of immunity to a neonate calf.

A more detailed study of the pathogen specific antibody activity in calf blood serum provided substantial additional information supplementing the Table VIII data. A detailed analysis of the Example 3 calf blood serum antibody activity is depicted in Table IX.

TABLE IX

EXAMPLE 3 - CALF BLOOD SERUM ANTIBODY TITERS

| | GROUP 1 Colostrum Fed | | | GROUP 2 Product Fed | | | GROUP 3 Product + Colostrum Fed | | |
|---|---|---|---|---|---|---|---|---|---|
| | DAYS POSTPARTUM | | | | | | | | |
| ORGANISM | 1 | 35 | 70 | 1 | 35 | 70 | 1 | 35 | 70 |
| IBR | 2 | 6 | 23 | <5 | 10 | 10 | <5 | 9 | 20 |
| B. abortus | 10 | 14 | 9 | <5 | 15 | 13 | <5 | 9 | 28 |
| Cl. perfringens | 55 | 10 | 27 | <5 | 22 | 22 | <5 | 17 | 63 |
| E. coli | 64 | 32 | 19 | <5 | 16 | 20 | <5 | 14 | 40 |
| H. somnus | 52 | 31 | 47 | <5 | 10 | 20 | <5 | 10 | 32 |
| S. dublin | 40 | 30 | 17 | <5 | 8 | 12 | <5 | 9 | 32 |

Table IX indicates that on the first day postpartum, the antibody titers of the colostrum fed calves substantially exceeded the antibody titers of either the product fed or product plus colostrum fed calves. As was the case with the Example 1 blood serum antibody titers depicted in Table V, the antibody titers of the colostrum fed calves decreased with time while the antibody titers of the product fed calves increased with time due to active production of antibodies by the calves. By seventy days postpartum, the immune performance of the Group 3 calves exceeded the essentially comparable immune system performance of the Group 1 and Group 2 calves. The Table IX analytical results indicated that the product of the present invention successfully performed as a substitute for high quality natural colostrum by ultimately yielding calf active immune system performance equivalent to that yielded by colostrum. This result is surprising and totally unexpected in view of the fact that the filtered product operated successfully at Ig concentration levels far below the minimum acceptable levels taught by the prior art. This result indicates that the filtered product contains immunologically active components which are either not present in natural colostrum or are present in substantially lower concentrations.

Table X-A depicts an analysis of the composition of Samples A, B and C of the filtered product produced in separate lots on different days. f

TABLE X-A

FILTERED PRODUCT COMPOSITION

| | PRODUCT SAMPLE | | |
|---|---|---|---|
| COMPONENT | A | B | C |
| Moisture (%) | 5.51 | 5.72 | 5.52 |
| True Protein (%) | 63.80 | 70.10 | 69.30 |
| Non-Protein Nitrogen (%) | .83 | .88 | .81 |
| Fat (%) | 4.10 | 5.92 | 5.25 |
| Lactose (%) | 19.70 | 11.80 | 14.90 |
| Ash (%) | 3.57 | 2.68 | 3.05 |
| Calcium (mM/kg) | 114 | 104 | 113 |
| Phosphate (mM/kg) | 32 | 16 | 22 |
| Sodium (mM/kg) | 99 | 88 | 93 |
| Potassium (mM/kg) | 213 | 148 | 180 |
| Ig/Protein (%) | 11.50 | 11.50 | 10.80 |
| Lactoferrin/Protein (%) | .50 | .22 | .67 |
| Lactoperoxidase/Protein (%) | .11 | 1.80 | .31 |

Table X-B depicts the Ig/lactoferrin complex Elisa titers of Samples A, B and C, the composition of which was analyzed in Table X-A.

TABLE X-B

FILTERED PRODUCT ELISA TITERS FOR Ig/LACTOFERRIN COMPLEX

| | ANTIBODY TITER | | |
|---|---|---|---|
| ORGANISM | A | B | C |
| IBR | 8000 | 7000 | 8000 |
| B. abortus | 8000 | 6000 | 15000 |
| Cl. perfringens | 8000 | 8000 | 16000 |
| E. coli | 16000 | 8000 | 16000 |
| H. somnus | 16000 | 8000 | 16000 |
| S. dublin | 8000 | 8000 | 16000 |

Table X-B indicates that the filtered product possesses significant levels of the immunologically active Ig/Lactoferrin complex.

Figure 6:
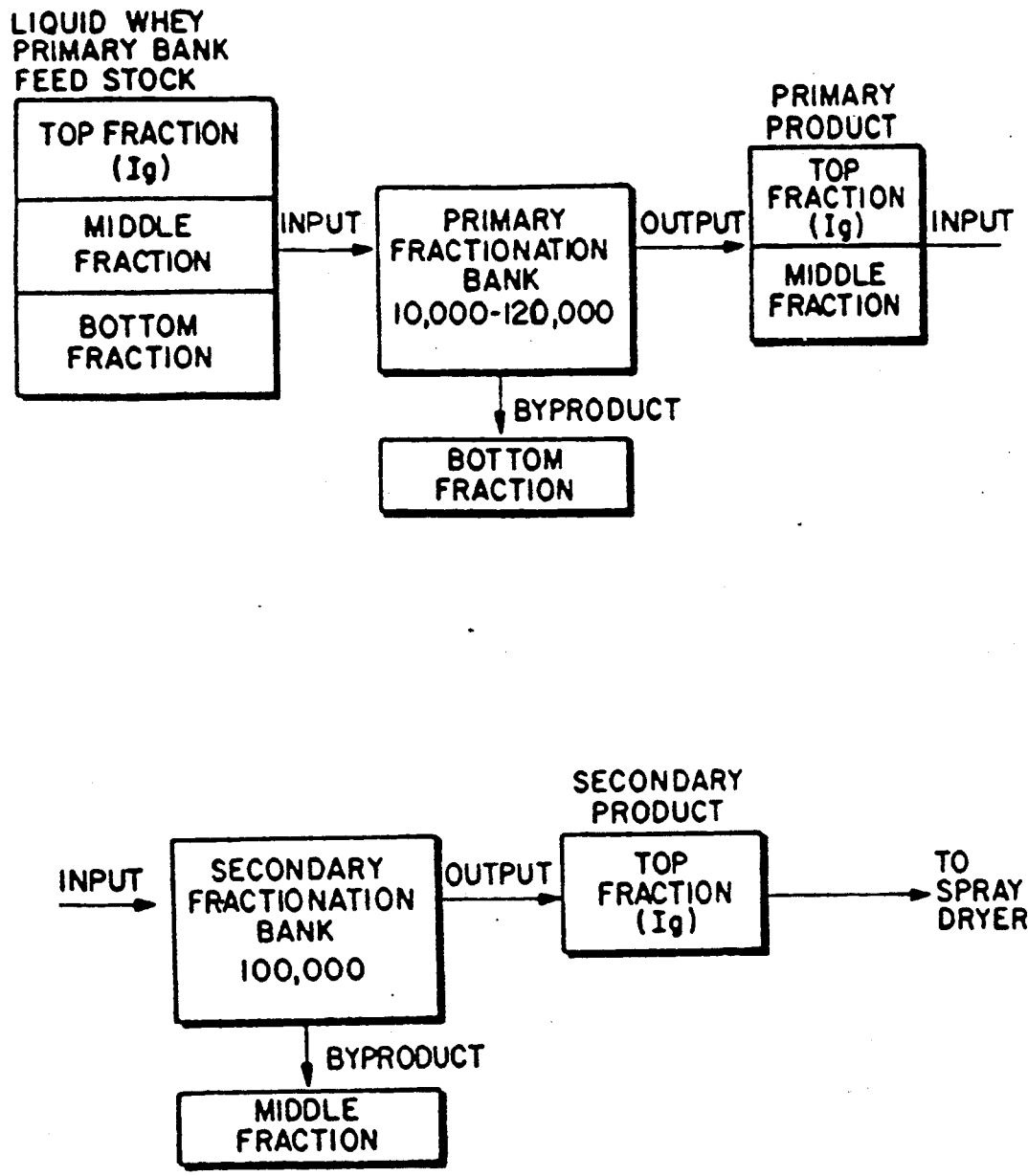
FIG. 6 represents a process flow diagram illustrating two stage processing of a liquid whey feedstock through a primary fractionation bank and a secondary fractionation bank.

Referring now to FIG. 6, a detailed example of the two-stage fractionation of whey will be described. The principals of this two stage fractionation process were explained above in connection with an initial fractionation of whey by a primary ultrafiltration bank utilizing one or more 10,000 Dalton membranes followed by a subsequent fractionation of the primary ultrafiltration bank retentate by a secondary ultrafiltration bank utilizing one or more 100,000 Dalton membranes.

As indicated by Table XI, whey includes 1) a zero to 8,000 Dalton bottom fraction including comparatively low molecular weight materials such as lactose and minerals; 2) an 8,000 to 70,000 Dalton middle fraction including lower molecular weight proteins such as alpha-lactalbumin, beta-lactoglobulin, serum albumin and lysozyme; and 3) a 70,000 to 400,000 Dalton top fraction including higher molecular weight proteins such as immunoglobulin, lactoferrin and lactoperoxidase as well as protein complexes. In a manner consistent with the terminology recited in Table XI, FIG. 6 indicates that liquid whey which serves as a primary fractionation bank feedstock consists of a bottom fraction, a middle fraction and a top fraction.

TABLE XI

WHEY FRACTION COMPOSTION

| FRACTION CLASSIFICATION | MOLECULAR WEIGHT RANGE | TYPICAL FRACTION SOLIDS COMPONENTS |
|---|---|---|
| TOP FRACTION | 70,000 TO 400,000 OR HIGHER | HIGH MOLECULAR WEIGHT PROTEINS INCLUDING IG, LACTOFERRIN LACTOPEROXIDASE AND PROTEIN COMPLEXES |
| MIDDLE FRACTION | 8,000 TO 70,000 | LOW MOLECULAR WEIGHT, NON-COMPLEXED PROTEINS INCLUDING ALPHA-LACTALBUMIN, BETA-LACTOGLOBULIN, SERUM ALBUMIN AND LYSOZYME |
| BOTTOM FRACTION | 0 TO 8,000 | LACTOSE, MINERALS, NON-PROTEIN NITROGEN |

An objective of the process of the present invention is to substantially enhance the concentration of the various immunologically active components of whey in a filtered product produced by the process of the present invention. Ig is widely recognized as having useful immunological functions as is the case with lactoferrin, lysozyme and lactoperoxidase. When the phrase "other immunologically active whey components" is used, it is intended to encompass non-Ig, immunologically active whey components including lactoferrin, lysozyme, and lactoperoxidase as well as other as yet unidentified immunologically active whey components.

The immunological activity of the primary and secondary ultrafiltration bank retentates is monitored and the relative immunological activity of such retentates is generally quantified by measuring and quantifying the immunological activity of Ig. Since Ig is the most heat sensitive immunologically active known whey protein, any degradation in the immunological activity of the Ig should reflect an overall degradation in the total immunological activity of the ultrafiltration retentates. As new immunological activity measurement techniques become available, such techniques could readily be adopted to measure the presence, distribution, potency and molecular weight of the known as well as presently unknown or unidentified immunologically active whey components.

Referring to Table XII below, the two-stage fractionation of whey in the primary and secondary fractionation banks depicted in FIG. 6 will now be described in detail. FIG. 6 represents a conceptual diagram illustrating the manner in which a primary fractionation bank yields a bottom fraction permeate and a combined top fraction/middle fraction retentate and in which a secondary fractionation bank yields a top fraction retentate and a middle fraction permeate. In the real world, no fractionation system is capable of yielding such idealized, pure fractions. Instead, a primary fractionation bank retentate or primary product will include substantially enriched concentrations of the whey top and middle fractions yet will also include reduced but significant concentrations of the whey bottom fraction. Similarly, a secondary fractionation bank retentate or secondary product will include a substantially enriched concentration of the whey top fraction, yet will also include reduced but significant concentrations of the whey bottom and middle fractions. Nevertheless, FIG. 6 accurately illustrates the process of the present invention on a conceptual level. The pilot plant data incorporated in Table XII indicates the manner in which the process of the present invention fractionates a liquid whey feedstock having an Ig concentration of 0.63 mg/ml.

The liquid whey feedstock was obtained following the clarification and separation stages of commercial cheese making operations as described above. The clarification and separation operations were carefully controlled to avoid significantly reducing the immunological activity of Ig molecules as described above. Such operations are preferably conducted at temperatures not exceeding about one hundred and five degrees Fahrenheit to meet this objective.

In the Table XII pilot plant run, a six stage ultrafiltration system functioned as the primary fractionation bank. Standard 10,000 Dalton polysulfone ultrafiltration membranes were utilized to separate the low molecular weight whey bottom fraction from the higher molecular weight whey middle and top fractions. The first four stages of ultrafiltration were conducted without diafiltration while the final two filtration stages were conducted with diafiltration.

As indicated by Table XII, the liquid whey feedstock was fractionated into a permeate having no measurable Ig concentration and into a primary product retentate having an Ig concentration of 18.5 mg/ml. The primary fractionation bank operated to increase the Ig to total solids ratio from 1.0% in the feedstock to 9.1% in the primary product while simultaneously increasing the 12.5% whey feedstock protein weight concentration to an 83% weight concentration in the primary product. None of the high molecular weight whey proteins were passed into the permeate or bottom fraction which consisted primarily of water, lactose, minerals and nonprotein nitrogen (NPN). By increasing the Ig to solids ratio from 1.0% to 9.1%, the primary fractionation bank provided a 910% Ig concentration enhancement.

The primary product served as the secondary bank feedstock and consisted predominantly of the whey middle and top protein fractions as demonstrated by the 83% primary product weight percent protein concentration.

The secondary fractionation bank utilized two ultrafiltration modules where each ultrafiltration module contained a spiral wound, 100,000 Dalton polysulfone ultrafiltration membrane. Such a membrane is designated by model number HFM-181 and is available from the Abcor Division of the Koch Corporation of Wilmington, Mass. Each ultrafiltration module was operated with diafiltration.

The ultrafiltration modules of the secondary fractionation bank were operated with an inlet pressure of 60 PSI and an outlet pressure of 20 PSI. The pH was controlled to a level of approximately 7.3. The peak secondary bank feedstock temperature was limited to 90° F. and the secondary fractionation bank residence time was minimized.

TABLE XII

| | FRACTIONATION PROCESSING RESULTS | | | | | |
|---|---|---|---|---|---|---|
| | PRIMARY FRACTIONATION BANK (10,000 Dalton) | | | SECONDARY FRACTIONATION BANK (100,000 Dalton) | | |
| PARAMETERS | LIQUID WHEY FEEDSTOCK | PERMEATE (Bottom Fraction) | RETENTATE (Primary Product) | SECONDARY BANK FEEDSTOCK | PERMEATE (Middle Fraction) | RETENTATE (Secondary Product) |
| Ig Concentration (mg/ml) | .63 | 0 | 18.5 | 18.5 | .05 | 36.4 |
| Ig as % of Total Solids | 1.0% | 0 | 9.1% | 9.1% | 1.92% | 15.8% |
| Ig as % of Protein | 8% | 0 | 10.9% | 10.9% | 2.75% | 17.87% |
| Weight % Proteins | 12.5% | 0% | 83% | 83% | 69.6% | 88.4% |
| Distribution of Total Solids | 100% | 87% | 13% | 100% | 11.5% | 88.5% |
| Distribution of Liquid Volume | 100% | 96.3% | 3.7% | 100% | 50% | 50% |

Table XII indicates that the secondary bank feedstock includes an Ig concentration of 18.5 mg/ml with an 83% protein weight concentration. The secondary fractionation bank divided this feedstock into a secondary product retentate having an Ig concentration of 36.4 mg/ml and into a middle fraction permeate having an Ig concentration of 0.05 mg/ml. The utilization of 100,000 Dalton ultrafiltration membranes enabled the secondary fractionation bank to retain most of the Ig, Ig/lactoferrin complexes, and other 100,000 Dalton and higher molecular weight immunologically active whey components while passing the lower molecular weight whey proteins into the permeate. The capability of the secondary fractionation bank to direct a substantial percentage of the lower molecular weight middle fraction proteins into the permeate and to direct a substantial percentage of the higher molecular weight top fraction proteins into the retentate is illustrated by the Table XII entries showing a 69.6 weight percent protein permeate concentration and an 88.4 weight percent protein retentate concentration. This separation of the middle and top fraction proteins increased the Ig to total solids concentration by 174% from 9.1% in the feedstock to 15.8% in the secondary product with only a comparatively minimal 1.92% being directed to the permeate. The primary and secondary fractionation banks together increase the Ig to total solids concentration by 1580% from 1% in the whey feedstock to 15.8% in the secondary product.

To be marketable, commercial food grade WPC must possess a minimum protein concentration of 35%. Since as indicated by Table XII, the secondary fractionation bank produces a permeate having a protein concentration exceeding 35%, the essentially non-immunologically active secondary bank protein rich permeate can be directly marketed as a commercial grade WPC product. The income derived from this WPC byproduct of the process of the present invention significantly reduces the net cost of the immunologically active secondary product.

Moisture was removed from the secondary product by spray drying operations of the type described above. Appropriate spray drying equipment may consist of a tower spray dryer having a high pressure nozzle and a cyclone collector. With such equipment, the inlet air temperature is controlled to a level of approximately 390° F. which results in an outlet temperature of between 160° to 180° F. The secondary product is dried to a moisture content of from four to six percent, preferably about five percent. Spray drying operations must be carefully monitored and controlled to avoid thermal deactivation of the Ig and other immunologically active whey components of the secondary product.

With prior art whey protein concentrate (WPC) processing techniques, a single stage ultrafiltration retentate is passed directly to an evaporator which is maintained at a temperature of 140° F. to 160° F. with a residence time of five to ten minutes to preheat the WPC prior to spray drying operations. Such evaporator preheating operations expose the WPC and any remaining immunologically active Ig to thermal conditions more than adequate to totally destroy any residual immunological activity.

In connection with implementation of the present invention, the residence time of the secondary product within the spray dryer should be minimized and the temperature controlled to prevent destruction of the biological activity of the Ig and other immunologically active whey components in the secondary product.

The dried secondary product from the spray dryer is stored and packaged in sealed containers to prevent moisture absorption.

In its dry form, a highly potent secondary product should preferably possess the following constituents on a percent of total solids basis: 1) protein concentration at least about seventy percent, preferably about eighty to eighty-five percent; 2) lactose plus minerals concentration of less than about thirty percent; 3) fat content of less than about six percent; 4) moisture content less than about six percent; and 5) an active Ig content of at least about seven percent. The immunological t activity of the Ig in the dry secondary product should be assayed to determine the concentration and distribution of immunologically active antibodies. Test procedures for implementing such Ig assays have been described above.

The protein to total solids concentration in the primary product can be varied from a concentration as low as thirty percent to a concentration as high as eighty-five percent. A short primary fractionation bank residence time and a limited number of intermediate ultrafiltration processing stages within the primary fractionation bank will produce a low protein to total solids concentration ratio while longer residence times and an increased number of intermediate ultrafiltration processing stages within the primary fractionation bank are necessary to approach an eighty-five percent protein to solids ratio. In implementing the process of the present invention, it is preferred that a final protein to total solids ratio of between sixty to eighty-five percent is attained and that more preferably a level of at least about seventy percent is attained to maximize the concentration of the Ig and other immunologically active whey components in the secondary product.

If the primary fractionation bank is designed and operated to produce a primary product having only a thirty to thirty-five percent protein to total solids concentration, comparatively high levels of lactose and minerals will also be present in the primary product. Such high levels of lactose and minerals may render such a primary product unfit for use as a passive immunity transfer product for neonate calves due to its potential to cause scours, severe dehydration and possible death.

With whey feedstock Ig concentrations of at least about 0.7 mg/ml, for example of about 0.7 to 1.2 mg/ml, the primary fractionation bank is capable of producing a primary product having a seven to ten percent Ig to total solids concentration which represents a level useful for numerous immune enhancing or immunity transfer operations.

The concentration of the Ig and other immunologically active whey components of the dry secondary product vary directly as a function of the concentration of the Ig and other immunologically active components present in the liquid whey feedstock. Selection of whey to maximize the concentration of the Ig and other immunologically active components is therefore important to reduce processing costs and to maximize the concentration of these components in the secondary product. Cheese processing operations are currently designed to produce either acid whey or sweet whey. Current cheese processing techniques produce an acid whey typically possessing near zero concentrations of immunologically active components. It is therefore desirable at the present time to use sweet whey produced by rennet precipitation of casein in implementing the present invention. The sweet whey/casein separation should preferably be carried out at a pH of from 6.5 to 4.6. Utilization of higher pH separation conditions within this range produces a higher concentration of immunologically active Ig in the resulting whey.

Sweet whey produced from various types of cheese processing operations results in varying Ig concentrations. In order of preference, sweet whey from the following cheese processing operations is preferred: 1) Swiss; 2) Mozzarella/Provolone; 3) cheddar; 4) Gouda; and 5) cottage cheese.

The concentration of Ig in whey varies directly with the concentration of Ig in milk. It has been found that the concentration of Ig in milk reaches its lowest level during the summer months and its maximum level during the winter months. Low potency summer whey must therefore be subjected to more extended ultrafiltration processing than is the case with more potent winter whey which in certain cases is acceptable for use after processing through the primary fractionation bank.

The concentration of Ig in whey will also vary on a day to day basis as a result of normal variations in the cheese making process. Processing time, processing temperatures and the level of microbial activity encountered during processing will all vary and potentially interact to cause changes in the Ig concentration in the raw whey feedstock. Standardization of the cheese processing parameters can minimize but typically not eliminate these day to day variations.

The concentration of Ig in the dry secondary product will also vary in response to changes in the fractionation processing parameters such as temperature, residence time, pump induced turbulence and microbial activity. As explained in detail above, it is always important to minimize the exposure of the Ig and other immunologically active whey components to high temperature operations and to minimize the residence time in such high temperature processing operations. Microbial activity should be controlled and minimized to the extent possible. Excessive microbial activity may result in significant pH drops during processing with resultant deactivation of the Ig and other immunologically active whey components. Unwanted microbial activity can be reduced by minimizing process residence time. It is therefore highly desirable to complete the secondary product drying operations within about four hours after the initial flash pasteurization implemented in connection with the cheese processing operation.

The concentration of the Ig and other immunologically active whey components can also be maximized by avoiding exposure of the whey to air and by avoiding or minimizing use of centrifugal pumps in the fractionation banks since centrifugal pumps both aerate and subject the pumped material to extreme mechanical turbulence. To the extent practical, positive displacement pumps should be used rather than centrifugal pumps.

The animal test data analyzed above indicate that the concentration of immunologically active Ig in the filtered product should possess a minimum concentration of about 7%, more preferably at least about 9% and most preferably greater than about 12% of the total solids. The specific embodiment of the two-stage fractionation process described above in connection with FIG. 6 yielded a filtered product having an Ig to solids concentration of 15.8%. Further refinements in the inventive process can yield Ig to solids concentrations of at least about 20% or at least about 35% or higher.

Although it was suggested above that a single 100,000 Dalton membrane could be utilized in the primary fractionation bank to directly separate the whey top fraction from the bottom and middle whey fractions, it has been found that the comparatively long whey proteins form a layered, mesh network or "dynamic membrane" on the inlet side of a 100,000 Dalton ultrafiltration membrane. Within ten minutes after commencement of filtration operations this dynamic membrane reduces the effective ultrafiltration membrane pore size from 100,000 Daltons to 10,000 Daltons. The primary fractionation bank can therefore separate the whey bottom fraction from the middle and top fractions, but it cannot separate the whey middle fraction from the top fraction regardless of the membrane pore size used. The dynamic membrane limits the capability of the primary fractionation bank to increase the concentration of Ig and other large molecular weight immunologically active whey components in the primary product.

The operation of the primary fractionation bank depicted in FIG. 6 and its separation of the whey bottom fraction from the combined whey middle and top fractions reconfigures the whey through mechanisms not currently understood. The reconfigured primary product can then be directed to the secondary filtration bank and its 100,000 Dalton ultrafiltration membranes without causing significant dynamic membrane problems and without significantly reducing the effective pore size of the 100,000 Dalton membranes. The 100,000 Dalton membranes of the secondary fractionation bank are now enabled to function at their design pore size and successfully operate to separate the whey middle fraction from the whey top fraction.

To successfully accomplish the function described above, the primary fractionation bank ultrafiltration membrane size is selected to ensure that the unwanted low molecular weight lactose, minerals and related whey components pass through the primary fractionation bank ultrafiltration membrane and are directed into the primary fractionation bank permeate. Ultrafiltration membranes having pore sizes on the order of at least about 10,000 to as high as about 120,000 Daltons may be used to accomplish this objective. Formation of a dynamic membrane on 100,000 or 120,000 Dalton primary fractionation bank membranes renders these comparatively large pore size membranes equivalent to a 10,000 Dalton membrane within a matter of minutes after filtration commencement.

The secondary product can be further processed by a tertiary fractionation bank to further increase the secondary product Ig concentration. The tertiary fractionation bank will typically take the form of an ultrafiltration system or a reverse osmosis unit to remove water from the secondary product and thereby further increase the Ig concentration in the tertiary fractionation bank retentate.

The utilization of a primary fractionation bank followed by a secondary fractionation bank as illustrated in FIG. 6 produces substantially enhanced results over those achieved through use of a primary fractionation bank by itself. The two stage fractionation process illustrated in FIG. 6 enables an immunologically active secondary product to be produced on a year-round basis even though the concentration of Ig in whey decreases significantly in the summer in comparison to other seasons. For certain uses of the immunologically active filtered product, such as transfer of passive immunity applications, a minimum weight of immunologically active Ig must be consumed by a neonate. As a result of the comparatively high concentrations of Ig in the secondary product produced by the FIG. 6 two stage processing operation, smaller doses of the secondary product can be dissolved in milk and fed to a neonate and still convey the minimum quantity of Ig, significantly reducing the per dose cost.

The immunologically active filtered product of the present invention can be used in many different applications. One specific application of the filtered product has been extensively described in connection with the transfer of passive immunity to neonate calves. Since pigs, goats, sheep and other domestic animals possess similar immunity transfer mechanisms, the filtered product may be used to transfer passive immunity to all such animals. In view of the fact that bovine antibodies have been demonstrated to be effective to counteract human antigens, the filtered product can be used in a disease resisting application to combat human diseases or to reduce the susceptibility of humans to selected diseases. The incorporation of a defined dosage of the filtered product into infant formula to increase the capability of an infant to resist disease represents a preferred human application of the filtered product. The filtered product may also be used as a feed supplement for either immature or adult domestic animals or as a food supplement for either immature or adult humans. The filtered product may t also be used to modify the colon or intestinal bacteria colonization or to control or reduce oral microbial colonization for the purpose of controlling the formation of oral plaque. Numerous other uses and applications of the filtered product of the present invention will be readily apparent to a person of ordinary skill in the veterinary, medical and immunology fields.

For disease resisting applications, a therapeutically effective quantity of the filtered product may be administered in either liquid or dry form. In its dry form, the filtered product may be packaged or encapsulated in a wide variety of enclosures or carriers well known to one of ordinary skill in the appropriate field. The product may be surrounded by an enteric coating to delay dispersion until arrival in the intestine. The product should not be exposed to excessive temperatures during packaging or encapsulation operations.

To date, the whey byproduct of cheese processing operations has almost uniformly been considered a troublesome, unwanted byproduct which caused serious waste disposal problems. To a limited extent, ultrafiltration systems have been implemented to recover immunologically inactive whey protein concentrate for use as a food additive.

As a result of the unique single or two stage whey fractionation techniques described above, the process of the present invention is able to produce a filtered product having controllable levels of immunologically active components from a raw whey feedstock. The concentration of immunologically active components in this filtered product has a demonstrated capability of transferring passive immunity to neonate calves and to therefore operate as a fully acceptable substitute for natural colostrum. Surprisingly, a relatively low concentration of Ig in the filtered product in combination with other immunologically active whey components has been shown to be as effective as or more effective than natural colostrum which possesses substantially higher Ig concentrations.

By nearly eliminating the highly adverse effects of the dynamic membrane, the two stage fractionation bank processing technique of the present invention is capable of producing a filtered product consisting primarily of the whey top fraction and having a significant concentration of Ig and other immunologically active whey components as well as a whey middle fraction byproduct which can be directly used as a commercially acceptable WPC food product.

The previously described examples demonstrate the ability of the active filtered product to protect newborn animals, to provide for their survival and general health, and to improve the general health of older animals. Enteric disease is one of the major threats to the health and life of newborns. Enteric infection and subsequent diarrhea is a health problem for animals of all ages and can negatively affect weight gain in growing animals.

It is known that diarrhea in animals, including humans, can be caused by a variety of different microorganisms (microbes). Commonly enteric disease may be caused by viruses, such as rotavirus or coronavirus, bacteria such as $E.\ coli$, campylobacter, citrobacter, and salmonella, and by protozoan parasites such as Cryptosporidia and coccidia. Other enteric disease, such as caused by Clostridia, may not be accompanied by diarrhea but still represent a serious health problem.

The active antibody content of the filtered product and the general health benefits derived from its use have been discussed above. Additional experiments were undertaken to demonstrate the effectiveness of the filtered product against specific organisms and its therapeutic benefits against an existing disease.

Further experiments have now been performed to demonstrate the effectiveness of the whey-derived filtered product in protecting calves from death and disease due to a K-99 $E.\ coli$ bacteria challenge and due to challenge with the protozoa Cryptosporidia.

In the K-99 $E.\ Coli$ experiment, thirty-seven calves were segregated into two groups of ten calves and one group of seventeen calves as illustrated in Table XIII below. Each calf was inoculated with a lethal dose of K-99 $E.\ coli$ culture (greater than $10^{10}$ pileated bacteria) from six to eight hours after birth and within about two hours after the initial feeding. The ten Group 1 calves were separated from their dams immediately after birth and received only a single initial feeding of ordinary milk instead of natural high Ig concentration colostrum.

The ten Group 2 calves were allowed to nurse colostrum from their dams for up to five hours after birth. Subsequent blood samples taken from these Group 2 calves demonstrated that the maternal colostrum had transferred high titers of K-99 $E.\ coli$ antibody to the calves.

The seventeen Group 3 calves were separated from their dams immediately after birth and received only a single 330 gram dose of seven percent Ig filtered product dissolved in milk.

All calves participating in this test received two quarts of milk twice daily for the duration of the experiment. Following administration of the K-99 $E.\ coli$ culture, all calves were observed every eight hours for five days. The calves were individually evaluated using a scoring system which assigned up to three points for severity of diarrhea, up to two points for dehydration and up to three points for depression (ability to stand or nurse). An animal showing no symptom in a category received zero points in that category.

Table XIII summarizes the results of this K-99 *E. coli* experiment and shows that: 1) seventy percent of the Group 1 calves died within five days after commencement of the experiment; 2) twenty percent of the Group 2 colostrum fed calves died; and 3) twenty-nine percent of the Group 3 seven percent Ig concentration filtered product-fed calves died.

TABLE XIII

| | K-99 *E. COLI* CHALLENGE | | |
|---|---|---|---|
| | CALF GROUP: | | |
| INPUT MATERIAL: | GROUP 1 MILK ONLY | GROUP 2 COLOSTRUM | GROUP 3 PRODUCT |
| No. of animals | 10 | 10 | 17 |
| % Mortality | 70 | 20 | 29 |
| Morbidity | 73.7 | 31.6 | 39.6 |

While there was a significant difference ($p=0.05$) in mortality between the Group 1 milk fed calves and the Group 2 and 3 calves which receiving antibodies via either colostrum or the filtered product, there was no significant statistical performance difference between the Group 2 colostrum fed calves and the Group 3 filtered product fed calves at the $p=0.05$ level.

Clinical symptoms resulting from the K-99 *E. coli* infection were observed to be significantly lower for the Group 2 colostrum fed calves and the Group 3 filtered product fed calves in comparison to the Group 1 milk fed calves. As between the Group 2 and Group 3 calves, no significant morbidity differential was observed at the $p=0.05$ level.

This K-99 *E. coli* challenge demonstrates that neonate calves fed the Ig-enriched filtered product of the present invention experienced significantly reduced mortality and clinically observed disease effects in comparison to calves consuming only ordinary milk containing only trace levels of Ig. No significant difference in either mortality or clinical disease-induced effects could be demonstrated between the Group 2 calves consuming natural colostrum and the Group 3 calves consuming the Ig-enriched filtered product of the present invention even though testing established that the natural colostrum contained high levels of K-99 *E. coli* antibody.

A second experiment was designated to measure the efficacy of the Ig-enriched filtered product against the protozoa Cryptosporidia, a microbe increasingly recognized as responsible for causing scours in young calves. This microbe also appears to be responsible for a growing incidence of parasitic infection in other domestic animals and in humans. The results of this test on animals are presumed to demonstrate product efficacy in animals other than calves such as humans.

As illustrated in Table XIV below, fifteen neonate calves were assigned to three groups of five each. The Group 1 calves received fresh maternal colostrum at initial feeding and a commercial milk replacer thereafter. The Group 2 calves were deprived of colostrum and instead received only a 454 gram dose of seven percent Ig-enriched filtered product of the present invention followed by a milk replacer during subsequent feedings. The Group 3 calves were treated the same as the Group 2 calves except that a ten percent of solids product concentration of the seven percent Ig filtered product was added to the milk replacer during the test. Each calf was infected with forty thousand Cryptosporidia oocysts three to four days after receiving the initial feeding of either colostrum or the filtered product. The results of this test are illustrated in Table XIV below:

TABLE XIV

| | CRYPTOSPORIDIA CHALLENGE | | |
|---|---|---|---|
| | CALF GROUP: | | |
| INPUT MATERIAL: | GROUP 1 COLOSTRUM | GROUP 2 PRODUCT (1 DOSE) | GROUP 3 PRODUCT (MULTIPLE DOSES |
| No. of animals | 5 | 5 | 5 |
| % Mortality | 0 | 0 | 0 |
| % Diarrhea | 80 | 20 | 20 |
| Diarrhea Duration In Days | 3 | 2 | 2 |

Four of the Group 1 colostrum fed calves developed diarrheal symptoms lasting from between two to four days averaging three days. Only one of the five calves in each Group 2 and Group 3 filtered product-fed calves developed diarrhea and then only for a period of two days. No bloody diarrhea occurred in either Group 2 or Group 3, but did occur in Group 1.

The Cryptosporidia challenge experiment confirmed that the Ig-enriched filtered product of the present invention was highly effective in treating infected calves while natural colostrum apparently provided no significant protective effect against Cryptosporidia. Because the Group 2 and Group 3 filtered product fed calves experienced significantly fewer and less severe diarrhea symptoms, this experiment establishes that the filtered product of the present invention includes one or more anti-microbial factors having high activity against the disease caused by Cryptosporidia protozoa, resulting in lower incidence and severity of symptoms. Although the Cryptosporidia experiment was limited to calves, it is presumed that the Ig-enriched filtered product of the present invention would be equally effective in treating similar microbial infections in other animals, including humans. The finding of effectiveness against Cryptosporidia is surprising and potentially very important, because there is currently no effective drug therapy for Cryptosporidia.

The results of the K-99 *E. coli* and Cryptosporidia experiments recited above demonstrate the high levels of efficacy of the Ig-enriched filtered product to these specific microbes. The results of these tests therefore establish that the filtered product of the present invention should have efficacy to either treat or prevent microbial infection not only from these two specific microbes, but also enteric infection with microorganisms of viral, bacterial or protozoal nature.

A third animal experiment was implemented to measure the efficacy of the filtered product in arresting chronic respiratory disease in postweaned Holstein heifers between two to six months old. This experiment was conducted at an operating dairy with twenty-two calves of mixed age all of which demonstrated symptoms of respiratory disease. The dairy owner stated that his heifers normally went through a respiratory disease stage resulting in some deaths before the surviving calves reached an age where they became either immune to or more tolerant to the respiratory disease. The dairy owner found this respiratory disease problem to represent a serious economic problem due to the death rate, medication cost, veterinary expense and reduced calf growth rate.

The twenty-two calves selected for this experiment were divided into two groups of eleven calves each. In assigning individual calves to each group, the size, age and severity of symptoms of each calf was considered to provide a relatively even balance between the calves placed in each group. The eleven Group 1 calves served as a control group while the eleven Group 2 calves were administered ten grams of a seven percent Ig filtered product per calf per day mixed with the daily feed ration of the calves. The calf weights varied from about one hundred and fifty pounds for the two month old calves to about four hundred and fifty pounds for the six month old calves.

The older calves in both groups looked worse than the younger calves and suffered deeper coughs and more abnormal lung sounds. All calves looked unthrifty and suffered from coughs, running eyes and noses, rough coats and droopy ears. The younger calves had apparently been infected after weaning. The older calves had been chronically ill and had received antibiotic treatment (Tylon) when necessary.

Ten days after commencement of this experiment, the calves were given a preliminary, non-medical examination. The Group 1 control calves continued to appear dull and unthrifty. The Group 2 product fed calves ate well and possessed smooth coats, both signs of superior health.

A veterinarian was called in on the tenth day of this test to medically assess the health of the calves of both groups and to attempt to diagnose the cause of the observed respiratory symptoms. He reported that seven of the Group 1 control calves had abnormal lung sounds indicating lung involvement in the existing respiratory infection. In the Group 2 product-fed calves, seven calves appeared to be cured of the respiratory disease in that they appeared bright and thrifty and evidenced no abnormal lung sounds. Although the remaining four Group 2 calves also possessed a bright and thrifty appearance, they continued to evidence some abnormal lung sounds, suggesting that they had greatly improved in health, but needed additional time to heal long-infected lung tissue.

At this point during the experiment, the seven Group 1 control calves with abnormal lung sounds and the three Group 2 product-fed calves with residual abnormal lung sounds were placed together in a single pen to form a third group. All ten Group 3 calves were treated with a ten gram daily dose of the filtered product. One of the original Group 1 control calves was selected for a study by necropsy, reducing the number of calves participating in the experiment from twenty-two to twenty-one calves.

After a second ten day period, the veterinarian returned and reexamined the ten product fed Group 3 calves. The lungs of seven of the ten Group 3 calves sounded normal indicating that they had been cured of respiratory disease. Two of the Group 3 calves had greatly improved in health with faint abnormal sounds evident in one lung only whereas previously both lungs had evidenced infection. The remaining uncured Group 3 calf, although appearing well and in good health, still evidenced some abnormal sounds in both lungs.

Thirty days after the completion of this twenty day test, the dairy owner was contacted and reported that all twenty-one of the heifers participating in the experiment were doing very well and evidenced no further signs of respiratory disease.

The ten gram per day dosage of seven percent Ig filtered product was demonstrated by this experiment to represent an adequate filtered product dosage level and represents an Ig to animal body weight ratio of about 0.001 grams of Ig per pound of animal body weight for the four hundred and fifty pound calves.

This third animal experiment demonstrates the efficacy of the immunologically active filtered product of the present invention in treating respiratory disease in postweaned calves. The results of this test therefore reasonably predict similar highly effective results in treating respiratory diseases in other animals, including humans.

Limited testing of the filtered product on human subjects has been conducted and has confirmed the antimicrobial efficacy of the filtered product in humans.

In a first human experiment, a five year old child having a natural immunoglobulin deficiency with a history of chronic gastrointestinal disease received orally by drinking or by nasogastric tube a dose of seventy grams of seven percent Ig content filtered product per day and remained disease free while continuing to consume daily dosages of the filtered product for several months. This child was confirmed to have Cryptosporidia associated with his intestinal cells, but did not shed oocysts or manifest disease symptoms during the term of this experiment.

In a second human experiment, a seventy-one year old, one hundred forty pound female had suffered persistent diarrhea over a period of three weeks in association with diverticulitis. After orally consuming twenty grams of a seven percent Ig-enriched filtered product in the morning and evening of a single day, the subject was found to be symptom free the following morning.

In a third human experiment, a thirty-three year old, one hundred forty pound female had suffered from diverticulitis induced chronic diarrhea over a period of several years. After consuming approximately eight grams of a seven percent Ig content filtered product morning and evening over a matter of days and continuing to maintain the same dosage level on an essentially continuous basis over a period of several months, this subject has been essentially symptom-free.

These three human experiments further confirm the efficacy of the Ig-enriched filtered product in treating gastrointestinal disease and diarrhea in humans.

As described above, the filtered product should periodically be tested or assayed to verify its immunological activity. Such testing can be accomplished in a variety of ways. The filtered product may be tested to measure the distribution and concentration of a number of pathogen specific antibodies. Alternatively, in most instances, testing may be accomplished to verify the presence and activity of only a single selected antibody. That selected antibody need not be pathogen specific to the enteric or respiratory disease sought to be treated. Preservation of at least a minimum level of activity of a single pathogen specific antibody has been found to be a highly reliable indication of the presence of a very broad range of immunological activity.

Based on the detailed description of a limited number of preferred implementations of the present invention and preferred methods of disease treatment, it will be apparent to those skilled in the art that the disclosed method of disease treatment using an Ig-enriched immunologically active whey fraction may be modified and expanded in a variety of ways and may be implemented in many related ways which would be readily apparent to persons of ordinary skill in the art. Accordingly, it is intended by the appended claims to cover all such modifications of the invention which fall within the true spirit and scope of the invention.

What is claimed is:

1. A process for transferring passive immunity to a neonate animal during a critical absorption period and for enhancing the initiation of active immunity in the animal comprising:
   a. providing whey concentrate derived from ordinary milk, the whey concentrate having an effective concentration of immunologically active immunoglobulin; and
   b. feeding a predetermined quantity of the whey concentrate to the animal during the critical absorption period such that the animal's blood serum immunoglobulin concentration is elevated to a level of about 1 mg/ml in response to ingestion of the predetermined quantity of the whey concentrate.

2. The process of claim 1, wherein the predetermined quantity of the whey concentrate fed to the animal includes a 0.055% ratio of immunoglobulin to animal weight.

3. The process of claim 1, wherein the whey protein concentrate is fed to the animal within 24 hours postpartum.

4. The process of claim 3, wherein the feeding step is commenced within 12 hours postpartum.

5. The process of claim 3, wherein the feeding step is commenced within 8 hours postpartum.

6. The process of claim 1, wherein the animal is a calf.

7. The process of claim 1, wherein the animal is a calf and wherein at least 25 grams of the immunologically active immunoglobulin is fed to the calf in no more than 600 grams of the whey concentrate for each 100 pounds of body weight.

8. The process of claim 1, wherein the whey concentrate is added to a liquid prior to feeding.

9. The process of claim 8, wherein the liquid is milk.

10. The process of claim 1, wherein the predetermined quantity of the whey concentrate is fed to the animal in a single dose in a liquid within 12 hours postpartum and wherein the weight of the immunoglobulin in the whey concentrate dose is equal to or greater than about 0.055% weight of the animal.

11. The process of claim 1, wherein the predetermined quantity of the whey concentrate is fed to the animal in a single dose in a liquid within 12 hours postpartum.

12. A process for preparing whey concentrate from ordinary milk, wherein the whey concentrate has at least 25 grams of immunologically active immunoglobulin in no more than 600 grams of the whey concentrate comprising:
   a. obtaining whey derived from ordinary milk, wherein the whey has a measurable but low level concentration of immunologically active immunoglobulin;
   b. ultrafiltering the whey through ultrafiltration means having an ultrafiltration membrane permeable to low molecular weight material including lactose and minerals, and a mean pore size of less than one hundred and sixty thousand daltons, for an effective amount of time to obtain a retentate protein concentration of about 70% weight concentrate;
   c. drying the retentate under thermal conditions which substantially preserve the EIA titer of the immunoglobulin in the whey to produce a filtered product wherein the filtered product has at least 25 grams of immunologically active immunoglobulin per 600 grams filtered product.

13. The process of claim 12, wherein the ultrafiltration membrane is a membrane having a pore size greater than about 1,000 daltons.

14. The process of claim 12, wherein the ultrafiltration membrane mean pore size is greater than about 10,000 daltons.

15. The process of claim 12, wherein the ultrafiltration membrane mean pore size is greater than about 100,000 daltons.

16. The process of claim 12, wherein a gel layer is formed on the ultrafiltration membrane in an amount to reduce the effective mean pore size to a level well below 160,000 daltons.

17. The process of claim 12, wherein the ultrafiltration step is accomplished within a first ultrafiltration unit to produce a first ultrafiltration retentate.

18. The process of claim 17, wherein the first ultrafiltration retentate is directed to a second ultrafiltration unit wherein the ultrafiltration step is continued to produce a second ultrafiltration retentate.

19. The process of claim 18, wherein the first ultrafiltration unit includes a first ultrafiltration membrane having a mean pore size of more than about 10,000 daltons and than about 160,000 daltons and wherein the second ultrafiltration unit includes a second ultrafiltration membrane having a mean pore size selected to retain substantially all immunoglobulin proteins while passing at least some of the lower weight molecular weight components of the first stage ultrafiltration retentate to thereby further increase the concentration of immunologically active immunoglobulins in the second ultrafiltration retentate.

20. The process of claim 12, wherein the method further comprises:
   a. ultrafiltering said whey through a second process stream including ultrafiltration means having an ultrafiltration membrane permeable to low molecular weight materials including lactose and minerals and with a mean pore size of less than one hundred and sixty thousand daltons until reaching a retentate protein concentration of at least about seventy percent weight concentration to yield a retentate having a substantially decreased concentration of lactose and minerals, said ultrafiltering step being accomplished under conditions which substantially preserve the EIA titer of the immunoglobulin in the whey;
   b. desalinizing said ultrafiltration retentate until the electrical conductivity of said retentate is not substantially above zero;
   c. passing said desalinized retentate through an ion exchange unit to produce an ion exchange product having a concentration of immunologically active immunoglobulin greater than about twenty percent;
   d. blending said filtered product of step "c" with said ion exchange product to produce a blended product having a concentration of immunologically active immunoglobulin greater than that of said filtered product and less than that of said ion exchange product.

21. The process of claim 20, wherein said diafiltration process is continued until the electrical conductivity of said ultrafiltration retentate is equal to or less than about three mMhos.

22. Whey protein concentrate produced by the process of claim 12.

23. A process for enhancing the health and growth rate of a domestic animal comprising the steps of:
   a. providing whey concentrate derived from ordinary milk, the whey concentrate having an effective concentration of immunologically active immunoglobulins; and
   b. feeding a predetermined quantity of the whey concentrate to the animal such that the animal's blood serum immunoglobulin concentration is elevated to a level of about 1 mg/ml in response to ingestion of the predetermined quantity of the whey concentrate.

24. The process of claim 23, wherein the weight of the immunoglobulin in the whey concentrate consumed daily by the animal is equal to or greater than about $1.9 \times 10^{-4}\%$ of the weight of the animal.

25. The process of claim 23, wherein an E.I.A. assay is used to assay the distribution and concentration of selected pathogen specific antibodies in the filtered product.

26. The process of claim 23, wherein a radial immune diffusion test is used to assay the weight concentration of immunoglobulin in the filtered product.

27. The process of claim 25, wherein a radial immune diffusion test is used to assay the weight concentration of immunoglobulin in the filtered product.

* * * * *